(12) United States Patent
Papineau et al.

(10) Patent No.: US 7,326,203 B2
(45) Date of Patent: Feb. 5, 2008

(54) DEVICE FOR ADVANCING A FUNCTIONAL ELEMENT THROUGH TISSUE

(75) Inventors: Paula Papineau, West Bridgewater, MA (US); Richard Pellegrino, Mendon, MA (US); John S. Crombie, East Hanover, NJ (US); Samit Patel, Maple Shade, NJ (US); Jeffrey Sutton, Medway, MA (US)

(73) Assignee: Depuy Acromed, Inc., Raynham, MA (US)

( * ) Notice: Subject to any disclaimer, the term of this patent is extended or adjusted under 35 U.S.C. 154(b) by 134 days.

(21) Appl. No.: 10/259,689

(22) Filed: Sep. 30, 2002

(65) Prior Publication Data

US 2004/0064136 A1    Apr. 1, 2004

(51) Int. Cl.
*A61B 18/18* (2006.01)
(52) U.S. Cl. ............................. 606/41; 606/86; 606/99; 606/104; 606/116; 606/32; 606/79; 606/80; 606/117
(58) Field of Classification Search .................. 606/41, 606/96, 79, 86, 104, 116–117
See application file for complete search history.

(56) References Cited

U.S. PATENT DOCUMENTS

| 5,643,319 | A | | 7/1997 | Green et al. |
| 5,693,052 | A | | 12/1997 | Weaver et al. |
| 5,849,011 | A | * | 12/1998 | Jones et al. ................... 606/47 |
| 6,016,452 | A | | 1/2000 | Kasevich et al. |
| 6,030,402 | A | * | 2/2000 | Thompson et al. ......... 606/185 |
| 6,190,383 | B1 | * | 2/2001 | Schmaltz et al. ............. 606/41 |
| 6,210,415 | B1 | * | 4/2001 | Bester ......................... 606/96 |
| 6,231,571 | B1 | | 5/2001 | Ellman et al. |
| 6,267,770 | B1 | * | 7/2001 | Truwit ........................ 606/130 |
| 6,280,441 | B1 | | 8/2001 | Ryan |
| 6,622,731 | B2 | * | 9/2003 | Daniel et al. ............... 128/898 |

FOREIGN PATENT DOCUMENTS

| EP | 05/84959 A | 3/1994 |
| EP | 1059067 A1 | 12/2000 |
| WO | WO 98/34550 | 8/1998 |
| WO | WO 01/01877 A | 1/2001 |
| WO | WO 01/57655 A2 | 8/2001 |

* cited by examiner

*Primary Examiner*—Linda C. M. Dvorak
*Assistant Examiner*—Matthew J. Kasztejna

(57) ABSTRACT

This invention relates to an apparatus for incrementally advancing functional probes through tissue.

11 Claims, 18 Drawing Sheets

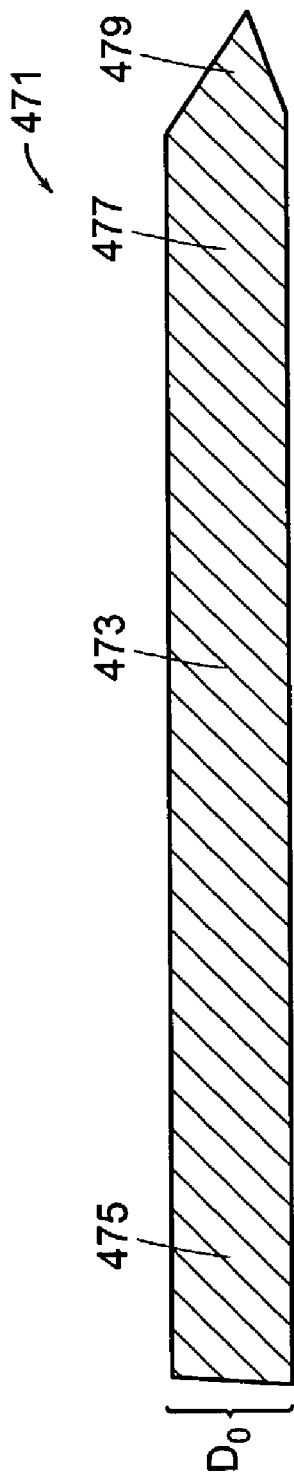
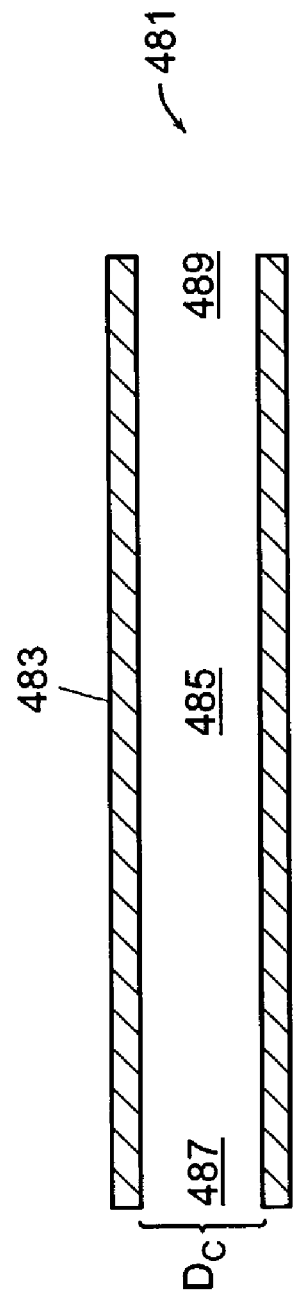
FIG. 12
FIG. 13

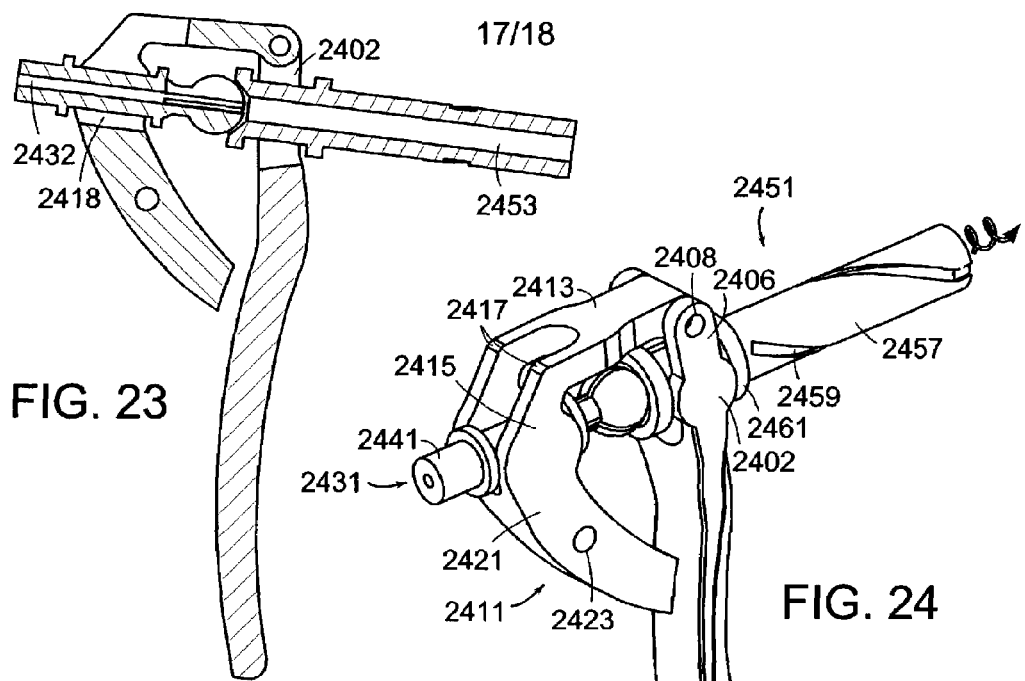
FIG. 23
FIG. 24
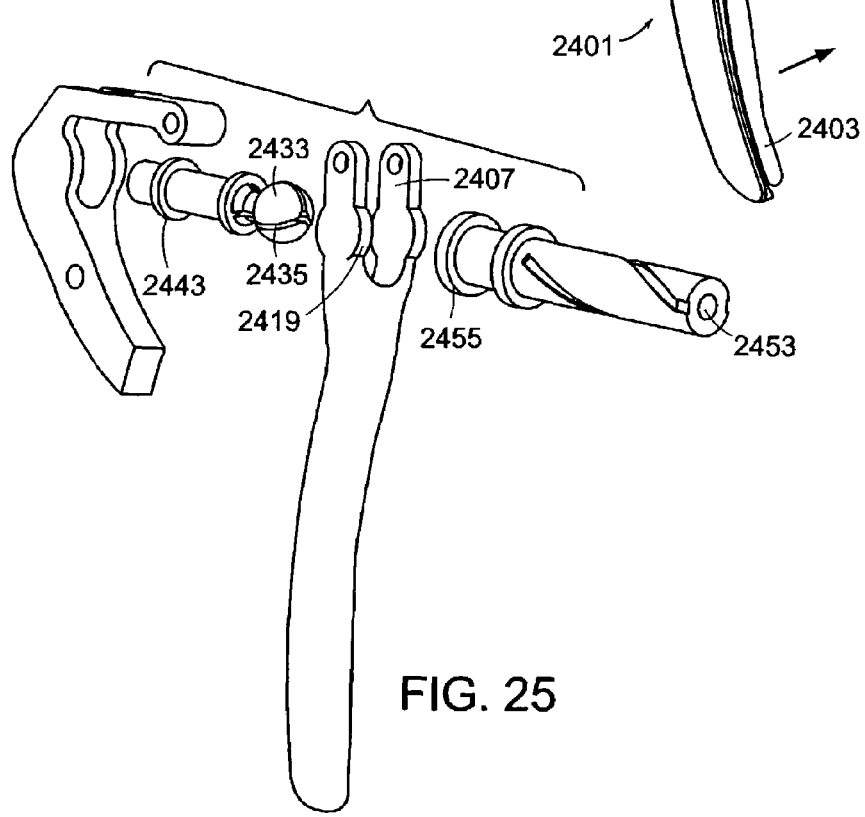
FIG. 25

DEVICE FOR ADVANCING A FUNCTIONAL ELEMENT THROUGH TISSUE

RELATED APPLICATIONS

This application is related to U.S. patent application Ser. No. 10/260,879 filed Sep. 30, 2002, entitled "Method Of Straddling an Intraosseous Nerve", the specification of which is incorporated by reference.

BACKGROUND OF THE INVENTION

In an effort to reduce back pain through early intervention techniques, some investigators have focused upon intraosseous nerves ("IONs") contained within the vertebral bodies which are adjacent the problematic disc, and the basivertebral nerve ("BVN") in particular.

For example, PCT Patent Publication No. WO 01/0157655 ("Heggeness") discloses ablating nerves contained within the vertebral body by first boring into the vertebral body with a probe, placing the tip of the probe in close proximity to the nerve, and then ablating the nerves with the tip. Heggeness discloses using laser devices, electricity transmitting devices, fluid transmitting devices and thermal devices, and devices for carrying either chemotherapeutic or radioactive substances as candidate probes. Heggeness further discloses multiple methods of accessing the ION. However, each of these methods essentially disclose either i) boring a straight channel into the vertebra such that placement of an electrode tip near the end of that channel will bring the electrode tip sufficiently close to the ION to effect its ablation, or ii) accessing the BVN via the vertebral foramen. None of these techniques disclose a mechanical means for advancing the probe.

EPO Patent Published Patent Application No. EP 1 059067 A1 ("Cosman") discloses ablative treatment of metastatic bone tumors, including those within the spine. Pain relief is reportedly achieved by penetrating the bone wall with a suitable probe, and applying heat through the probe to ablate either the bone tumor or the tissue near the bone tumor. Cosman also teaches that the treatment may also be used to ablate the nerves and nerve ramifications in and/or around the bone to desensitize them against further tumor encroachment. See Cosman at col. 11, lines 7-11. Cosman discloses probe devices whose electrodes can deviate from the axis of the access channel. In particular, Cosman discloses steerable tips, spring-like electrodes that take a straight shape within the catheter and then curve upon exiting the catheter. Cosman discloses that the curved portion of the electrode may be a rigid and rugged permanent curve, or it may be a flexible configuration so that it can be steered, pushed or guided by the clinician to be positioned at various location. See Cosman at 8,40-50. Again, none of these techniques disclose a mechanical means for advancing the probe.

In percutaneous procedures, (such as those described by Heggeness), imaging techniques (such as fluoroscopy) is typically employed by the clinician in order to accurately place the probe tip at the desired location. However, since exposure to radiation (such as X-rays) should be minimized, the clinician typically uses the fluoroscope only on an intermittent basis during a procedure, but not as a direct visualization aid in positioning the probe. That is, the clinician may place his or her hands in the fluoro field and move the probe "in the dark", move out of the imaging field, activate the imaging device, check the probe location under active imaging, inactive the imaging device, place his or her hands in the radiation field and move the probe "in the dark", etc. The failure to move the probe under direct imaging guidance may result in imprecise positioning of the probe, as the clinician's subjective feel plays a large role in estimating how a probe has been moved in the dark.

Moreover, since conventional RF probe heats only about a 1 cc volume in bone, the amount of imprecision associated with placing probes in the dark may affect the clinician's ability to locate a probe sufficiently close to a nerve in order to therapeutically treat the nerve.

Therefore, it is one object of the present invention to provide an apparatus that provides the clinician with more control over probe placement and location in electrode-related percutaneous procedures.

U.S. Pat. No. 6,280,441 ("Ryan") discloses an RF electrode ablation probe having a housing and a semirigid, helical probe extending distally from the housing and having a sharpened distal tip. The probe advances into the patient by rotation relative to the housing, thereby twisting into the patient.

Ryan does not disclose a system wherein the distal tip of the probe is sufficiently sharp to pierce bone, wherein the probe can advance distally relative to its housing, wherein the distal portion of the probe is adapted to pass through the housing, nor wherein the outer surface of the probe has teeth adapted for ratcheting.

U.S. Pat. No. 6,210,415 (Bester) discloses a surgical drill guide having a guide tube advancable distally by a ratchet and pawl mechanism, wherein the distal end of the guide tube has a pair of pins. However, Bester does not disclose an apparatus having an electrode.

U.S. Pat. No. 6,016,452 ("Kasevich") discloses an RF electrode system for use in the prostate, wherein actuating members 58,60 are mounted for reciprocal longitudinal movement relative to housing 52 to selectively move a plurality of electrodes between nondeployed position (in which the distal end of the electrode is within the housing) and a fully deployed position (in which the distal end of the electrode extends from the housing) (5,44-46). In one embodiment, longitudinal movement of actuating members 58,60 causes corresponding conjunctive movement of electrodes 72a-c.

Kasevich does not disclose a system wherein the probe has a tip sufficiently sharpened to pierce bone. There is no provision for incremental distal advance of the electrode within the housing—simply actuation between one deployed and one nondeployed position. Kasevich does not disclose a system wherein the housing is adapted to allow the distal end of the probe to fully pass through the housing. Kasevich does not disclose a probe having an outside surface having teeth adapted for ratcheting.

U.S. Pat. No. 6,030,402 (Thompson) discloses an instrument for penetration of tissue including a penetration member and a distal backstop for limiting the penetration depth of the penetration member. Thompson further discloses advancing the penetration member and a distal backstop by a ratchet and pawl mechanism.

However, Thompson does not disclose an instrument having an electrode.

U.S. Pat. No. 6,231,571 ("Ellman") discloses a probe having an electrode connected to a pull wire to allow the distal end of the probe to change direction. However, Ellman does not disclose an apparatus in which the probe may be distally advance relative to the housing.

U.S. Pat. No. 6,190,383 ("Schmaltz") discloses an apparatus for thermal treatment of tissue comprising a plurality of electrodes that are rotatable about an elongated housing.

The preferred tissue site is a myoma. The electrodes may include an external threaded portion 72 dimensioned to facilitate advancement and retention of the electrode in the tissue. Each electrode further possesses a sharpened distal end to facilitate penetration through tissue. Activation of a motor causes rotation of the drive shaft and advancement of the needle electrodes within the myoma. An axial force may be applied by the surgeon to the apparatus to facilitate insertion within the tissue.

U.S. Pat. No. 5,693,052 ("Weaver") discloses an electrosurgical instrument for use in bipolar electrosurgery, including a probe having a nickel-free high chromium coating.

However, neither Ellman, Schmaltz nor Weaver disclose an apparatus in which the probe may be distally advanced relative to a housing.

In sum, the prior art does not appear to disclose a device designed to penetrate bone, is incrementally distally advanceable through the bone, and can therapeutically treat the bone.

SUMMARY OF THE INVENTION

In some preferred embodiments, the present invention relates to a device, advantageously used for therapeutically treating bone, which comprises a) a probe having an functional element, and b) an advancement mechanism adapted to advance the probe into the bone with mechanical advantage.

The present invention is advantageous because it not only provides the clinician with a functional element (preferably an electrode) capable of therapeutically treating bone, it further provides the clinician with a capability to advancing the probe into the bone with mechanical advantage, thereby improving control of the device. Advancing with mechanical advantage allows the clinician to focus his or her efforts upon probe orientation, and not simply the need to exert enough force to penetrate the hard cortical shell of the target bone.

This present invention represents an advance over conventional bone-related therapeutic probes, as these probes have no capability to distally advance the probe into the bone with mechanical advantage. This present invention also represents an advance over conventional bone-related probes capable of advancing with mechanical advantage, as these probes have no capability to therapeutically treat the bone.

Therefore, in accordance with the present invention, there is provided a device for therapeutically treating bone, comprising:
a) a housing having a base portion having a distal face, and a first passage opening upon the distal face and forming a longitudinal axis,
b) a probe adapted to advance through the first passage along the longitudinal axis, the probe having a functional element thereon, and
c) an advancement mechanism adapted to advance the probe through the first passage with mechanical advantage.

In some preferred embodiments, the present invention relates to a device, advantageously used for therapeutically treating bone, which comprises a) a probe having an functional element, and b) an advancement mechanism adapted to incrementally advance the probe into the bone.

The present invention is advantageous because it not only provides the clinician with a functional element (preferably an electrode) capable of therapeutically treating bone, it further provides the clinician with a capability to incrementally advance the probe into the bone, thereby improving control of the device. The incremental advance capability allows the clinician to advance the probe by a known amount with only intermittent imaging.

This present invention represents an advance over conventional bone-related therapeutic probes, as these probes have no capability to incrementally distally advance the probe into the bone. This present invention also represents an advance over conventional bone-related probes capable of incremental advancement, as these probes have no capability to therapeutically treat the bone.

Therefore, in accordance with the present invention, there is provided a device for therapeutically treating bone, comprising:
a) a housing having a base portion having a distal face, and a first passage opening upon the distal face and forming a longitudinal axis,
b) a probe adapted to advance through the first passage along the longitudinal axis, the probe having a functional element thereon, and
c) an advancement mechanism adapted to incrementally advance the probe through the first passage.

In some preferred embodiments, the present invention relates to a device, advantageously used for therapeutically treating bone, which comprises a) a probe having an functional element, and b) an rotation mechanism adapted to rotate the probe.

The present invention is advantageous because it not only provides the clinician with a functional element (preferably an electrode) capable of therapeutically treating bone, it further provides the clinician with a capability to rotate the probe, thereby improving the directional control of the device.

This present invention represents an advance over conventional bone-related therapeutic probes, as these probes have no capability to rotate the probe. This present invention also represents an advance over conventional bone-related probes capable of rotating the probe, as these probes have no capability to therapeutically treat the bone.

Therefore, in accordance with the present invention, there is provided a method of placing a probe in bone, comprising the steps of:
a) providing a device for therapeutically treating bone, comprising:
  i) a housing having a base portion having a distal face, and a first passage opening upon the distal face and forming a longitudinal axis,
  ii) a probe adapted to advance through the first passage along the longitudinal axis, the probe having a functional element thereon, and
  iii) an advancement mechanism adapted to advance the probe through the first passage,
b) inserting the probe into a bone,
c) actuating the advancement mechanism to advance the probe in the vertebral body, and
d) rotating the probe about the longitudinal axis.

Also in accordance with the present invention, there is provided a preferred device for therapeutically treating tissue, comprising:
a) a housing comprising:
  i) a base portion having a proximal side and a distal side, and
  ii) a first passage extending through at least the distal side forming a distal opening (and preferably through the proximal side forming a proximal opening and a throughbore), the first passage defining a longitudinal axis, b) a probe having:
  i) an outer surface adapted to advance distally within the first passage along the longitudinal axis,
  ii) a distal end adapted to advance distally relative to the distal opening of the housing (preferably, adapted to advance through the distal opening of the housing), the distal end preferably shaped to penetrate bone, and
  iii) a functional element thereon (preferably an electrode), and further preferably having teeth along the outer surface adapted for racheting, and
c) an advancement mechanism (preferably a ratchet and pawl mechanism) adapted to distally advance (preferably by translation, preferably linearly) the probe relative to the first passage.

DESCRIPTION OF THE FIGURES

FIGS. 12 and 13 respectively disclose cross sectional views of a stylet and a cannula used in accordance with the present invention.

FIG. 23 discloses a cross sectional view of a preferred advancement mechanism capable of creating probe rotation upon advancement, the mechanism comprising a collet and a sleeve.

FIG. 24 discloses a perspective view of a preferred advancement mechanism capable of creating probe rotation upon advancement, the mechanism comprising a collet and a sleeve.

FIG. 25 discloses an exploded view of FIG. 24.

DETAILED DESCRIPTION OF THE INVENTION

Figure 1:
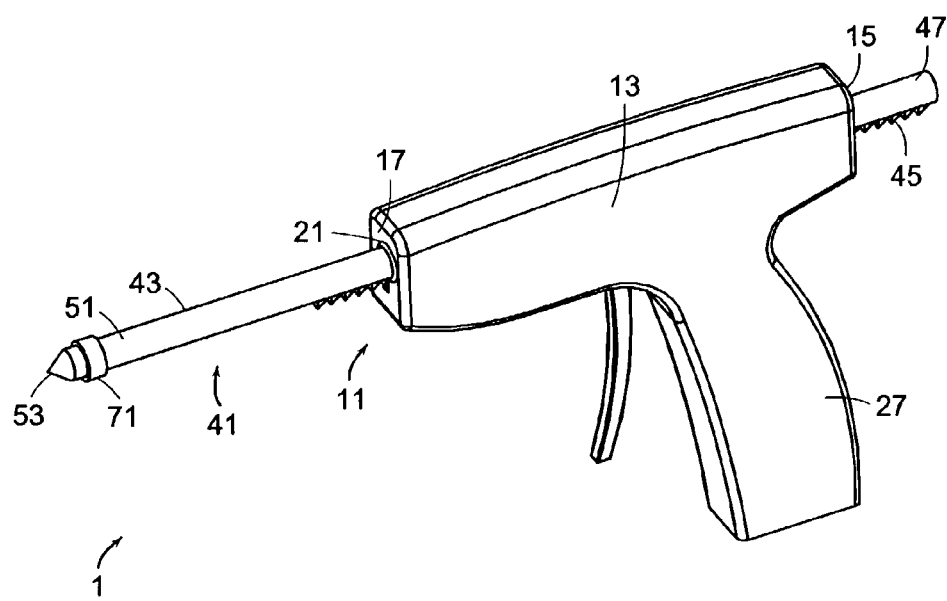
FIG. 1 discloses a perspective view of a first embodiment of the device of the present invention.
Figure 2:
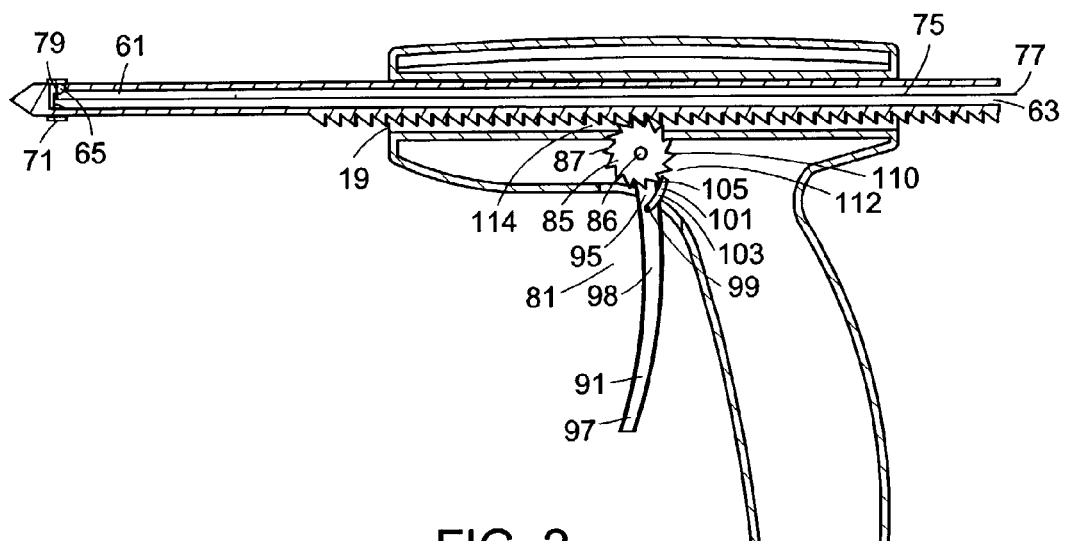
FIG. 2 discloses an axial cross section of FIG. 1
Figure 3:
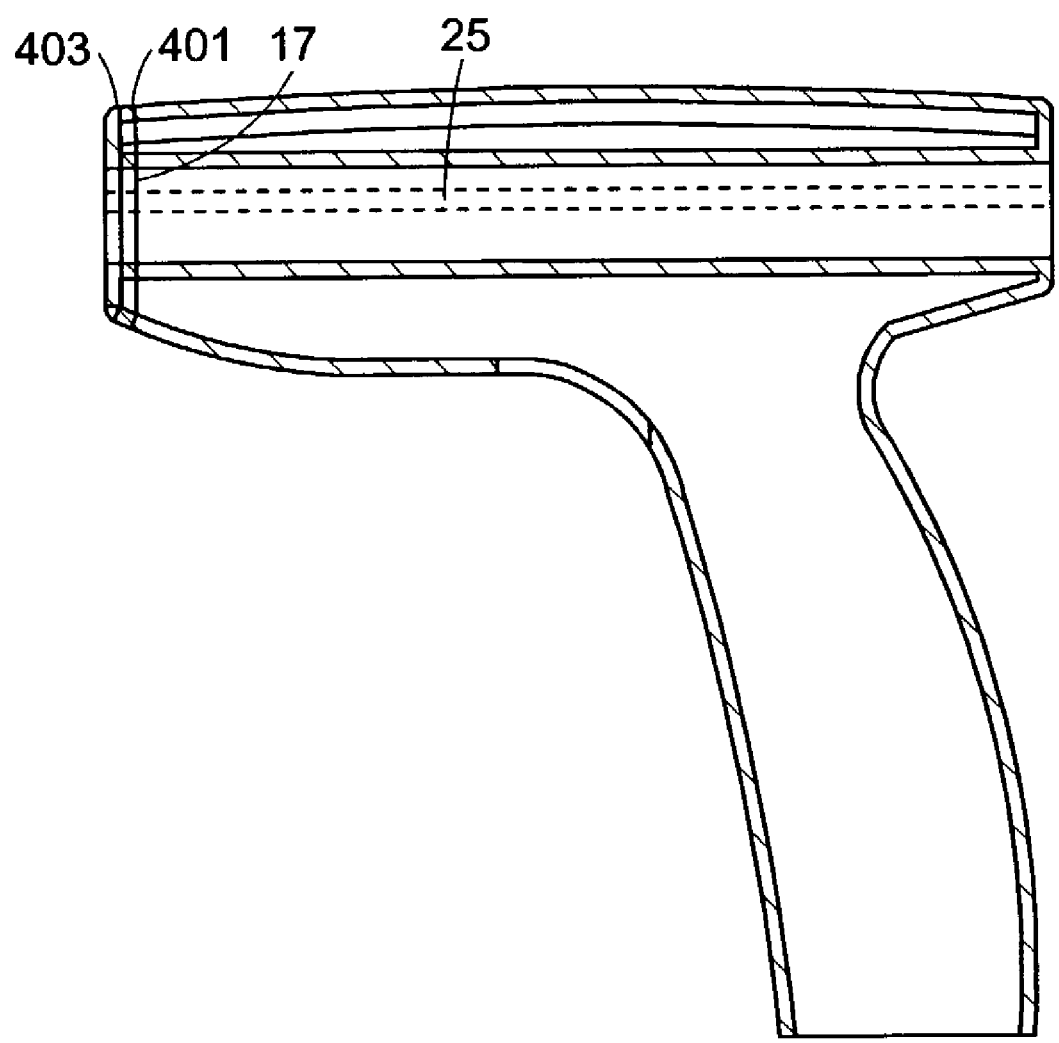
FIG. 3 discloses a cross-section of a housing of the present invention having adhesive and a patch attached to its distal face.

Now referring to FIGS. 1-3, there is provided a device 1 for therapeutically treating tissue, comprising:
a) a housing 11 comprising:
  i) a base portion 13 having a proximal side 15 and a distal side 17, and
  ii) a first passage 19 extending through the distal side forming a distal opening 21 and through the proximal side forming a proximal opening 23 and a throughbore 25, the first passage defining a longitudinal axis A, and
  iii) a grip extending 27 from the proximal end portion of the housing,
b) a probe 41 having:
  i) an outer surface 43 adapted to advance distally within the first passage along the longitudinal axis and having a first plurality of teeth 45 formed therealong and adapted for ratcheting,
  ii) a proximal end portion 47,
  iii) a distal end portion 51 adapted to advance distally relative to the distal opening of the housing and advance through the distal opening of the housing, the distal end portion having a tip 53 shaped to penetrate bone, and
  iv) a bore 61 formed therewithin and extending from the proximal end and forming a proximal opening 63 and terminating in the distal end portion at a distal opening 65,
  v) a functional electrode element 71 located at the distal end portion of the probe,
  vi) a electrical wire 75 having a proximal end 77 extending from the proximal opening of the proximal opening and a distal end 79 in electrical connection with the electrode,
c) a ratchet and pawl advancement mechanism 81 adapted to incrementally distally advance the probe relative to the first passage, the ratchet and pawl advancement mechanism comprising:
  i) a ratchet wheel 85 having a centerpin 86 pivotally attached to the housing proximal to the grip, and a circumference having a second plurality of teeth 87 formed thereon shaped to engage the first plurality of teeth,
  ii) a lever 91 having a first end portion 95 pivotally attached to the ratchet wheel centerpin and a second end portion 97 having a shape adapted for gripping, and having an outer surface 98 having a pin 99 extending therefrom, and iii) a pawl 101 having a first end 103 pivotally attached to the pin of the lever and a second end 105 shaped for engaging the second plurality of teeth.

Generally, the housing comprises:
 i) a base portion having a proximal side and a distal side, and
 ii) a first passage extending through at least the distal side forming a distal opening, the first passage defining a longitudinal axis.

Preferably, the housing should have a shape suitable for accommodating the incremental advance therein of the probe. Any conventional housing shape, such as those used in conventional caulk guns, may also be used.

In some embodiments, the passage forms a single distal opening adapted for advancement of the probe therein. Preferably, however, the passage forms two openings upon opposing sides of the housing, thereby forming a throughbore. In this condition, the distal end of the probe can be conveniently loaded through the proximal opening of the housing, advanced through the housing, and exit through the proximal opening.

Therefore, in accordance with the present invention, there is provided a device for therapeutically treating bone, comprising:
a) a housing having a base portion having a distal face, and a first passage opening upon the distal face and forming a longitudinal axis,
b) a probe adapted to advance through the first passage along the longitudinal axis, the probe having a functional element thereon, and
c) an advancement mechanism adapted to advance the probe through the first passage.

Preferably, this housing throughbore is substantially linear in order to accommodate substantially linear probes.

In some embodiments, the passage may comprise a laterally-disposed or vertically-disposed slot that runs along at least a portion of the longitude of the passage, so that the probe can be side-loaded or top-loaded into the housing. In some embodiments, this slot runs the entire length of the passage. In some side-loading embodiments, and now referring to FIG. 2, centerpin 86 is designed to ride in a slot, thereby allowing the ratchet wheel 85 to be disengaged and facilitate the side loading.

In some embodiments, the housing further comprises a handle portion (or grip) extending from the base portion. Preferably, this grip extends from the lower side of the housing in a direction substantially similar to the direction of the lever. This handle portion helps the clinician maintain control of the housing during actuation, and allows single handed actuation of the lever.

In some embodiments, the device further comprises at least one anchor. In some embodiments, this anchor is adapted to be anchored into the patient's skin, thereby helping maintain control of the housing during use and providing the clinician with fixed coordinates. In other embodiments, the anchor is adapted to be anchored to an external apparatus, thereby insuring a minimum of movement during the procedure. In other embodiments, the anchor is adapted for bony fixation so that it can be anchored to the patient's bone (such as the transverse or spinous process), so that the device can move along with any natural movements of the patient, such as those caused by breathing.

Therefore, in accordance with the present invention, there is provided a device for therapeutically treating bone, comprising:

a) a housing having a base portion, a distal face and a first passage opening onto the distal face and forming a longitudinal axis,
b) a probe adapted to advance through the first passage along the longitudinal axis, the probe having a functional element thereon,
c) an advancement mechanism adapted to advance the probe through the first passage, and
d) an anchor rotatably attached to the distal face of the housing and adapted to provide rotation of the housing about the longitudinal axis.

In some embodiments, the anchor comprises an adhesive. Now referring to FIG. 3, in some embodiments, the housing further comprises a distal face having an adhesive 401 disposed thereon. In use, the clinician may advantageously press the adhesive onto the patient's skin in order to fix the position of the device. Preferably, a non-adhesive patch 403 is disposed upon the adhesive to protect the adhesive from adhering to undesired surfaces prior to use. Preferably, the patch is removed by the clinician, thereby exposing the underlying adhesive, immediately prior to placing the device on the patient's skin.

In some embodiments, the anchor comprises a separate piece to be connected to the housing and adapted to provide the clinician with a fixed position on the patient's back.

Figure 4:
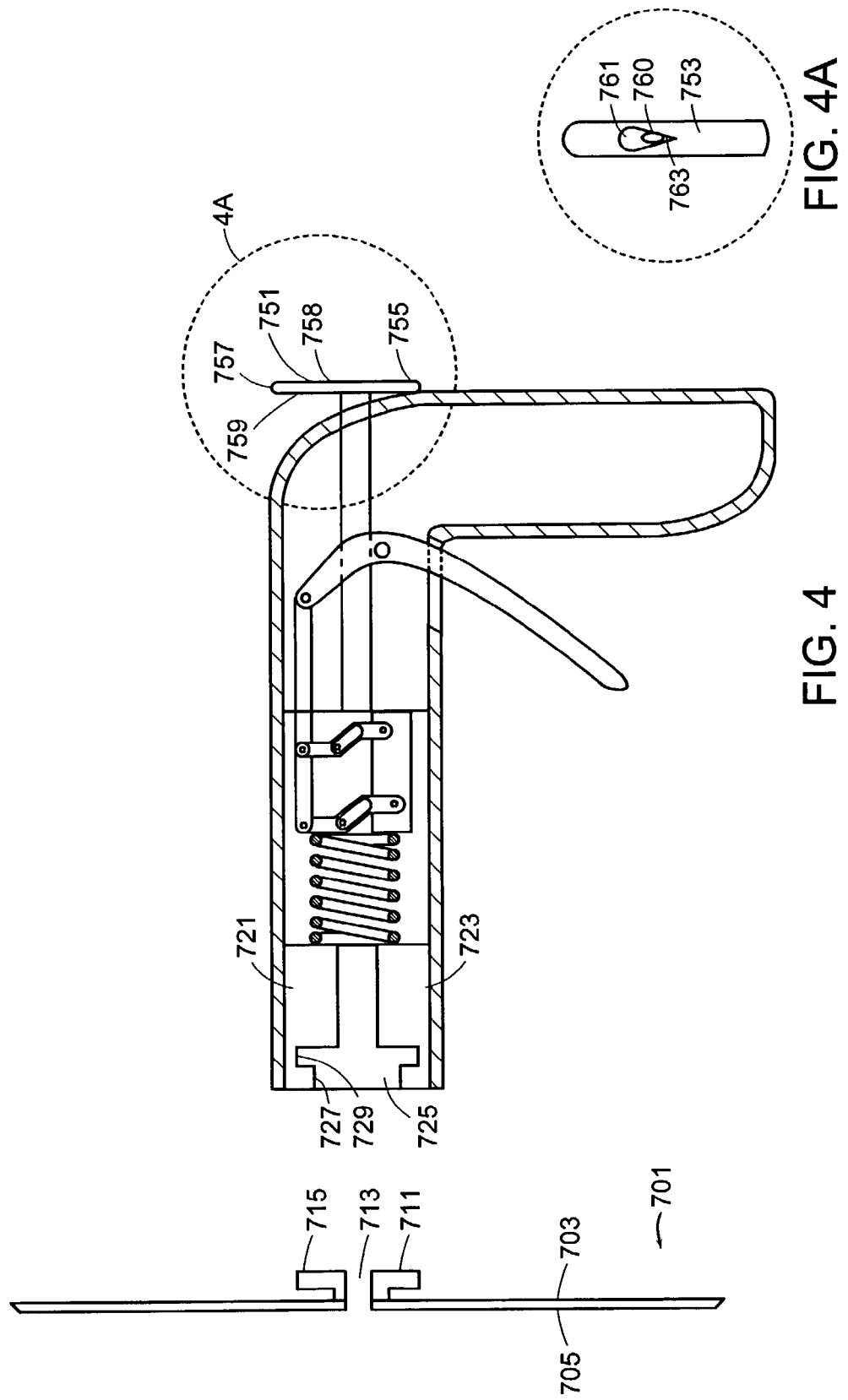
FIG. 4 discloses an exploded cross-section of a housing and an anchor of the present invention.

In one preferred embodiment thereof, and now referring to FIG. 4, the anchor comprises:
 a) a plate 701 having a proximal face 703, a distal face 705 adapted to conform to the patient's back, and a throughhole 713 extending from the proximal face to the distal face, and
 b) an annulus 711 extending proximally from the proximal face, formed around the throughhole and having a laterally extending proximal lip 715.

In conjunction with the anchor, the distal end 721 of the housing 723 further comprises a recess 725 adapted for receiving the annulus of the anchor. In preferred embodiments, the recess surrounds the distal end of the first passageway. More preferably, the recess extends laterally from the first passageway.

This inventive anchor is advantageous because the entry point for the probe is now fixed, and the clinician may now proceed from fixed coordinates.

In some embodiments, the anchor is adapted to prevent rotation of the housing about throughhole 713.

In some embodiments wherein the anchor attaches to bone, the surface area of the plate is sufficiently large so that it suitably reduces the pressure experienced by the surrounding bone so that the clinician need not be concerned about fracturing the surrounding bone when a force sufficient to breach the bone is applied to the probe.

In some clinical settings, the clinician may find it useful to rotate the probe about its longitudinal axis. For example, a probe may comprise an articulated tip which, when deployed, helps the surgeon steer the probe. The steerability of such a probe may be greatly enhanced if the clinician were able to rotate the probe prior to tip deployment. In another example, the probe may have a functional element whose face is disposed on a lateral wall (such as a side port). The ability to direct the face of the functional element in a given direction may be greatly enhanced if the clinician were able to rotate the probe.

Therefore, in preferred embodiments, the anchor and the distal recess are adapted so that, when the anchor is disposed within the recess, the housing can be at least partially rotated about throughbore 713, preferably 360 degrees about the throughbore. In some embodiments, the recess has a distal threaded portion 727 adapted to receive the annulus lip therein, and a widened proximal portion 729 adapted to accommodate rotation of the lip. When the anchor is threaded onto the recess, the lip moves proximally through the threaded proximal portion and into unthreaded proximal portion 729. This preferred anchor is advantageous because, since the annulus lip can freely rotate in a 360 direction within the recess, the entire housing can be rotated in any direction within the plane parallel to the plate. This rotational freedom allows the clinician to steer the probe in directions that deviate from the longitudinal axis of the first passage. For example, a probe having a distal bend could be incrementally advanced a first distance through the device; the housing could be than rotated in a desired direction, and the probe could then be further incrementally advanced. This rotational freedom also allows the clinician to correct a misdirected probe. For example, an ultrasound probe having masking that provided only 90 degrees of firing could be redirected in-situ.

In some rotational embodiments, the anchor can comprise a bearing race. In other rotational embodiments, the anchor can comprise a means for incrementally rotating the housing.

In some embodiments, the recess may be spherical shaped. This provides free rotation in the x-y and z planes. However, if the probe is not thereafter locked into position after the desired entry angle has been obtained, the probe may bind or kink during use.

In some embodiments, the anchor can further comprise a locking means. The locking means is useful when the rotational capability of the anchor is used to rotate the probe about its longitudinal axis, and the clinician desires to retain the new orientation provided by the rotation. The locking means allows the clinician is indefinitely retain the new orientation of the probe. In some embodiments, the locking means may comprise a screw adapted to pass through a thread hole located in the housing and bear against the anchor, thereby frictionally locking the anchor to the housing.

When directing a probe into tissue, the clinician typically has an understanding of the desirable angle of entry of the probe, but must rely upon inexact manual insertion in order to place the probe at the desired entry vector. Likewise, the clinician may further have an understanding of the desirable degree of rotation of the probe, but again must rely upon inexact manual rotation in order to orient the probe to a desired orientation.

Accordingly, it would be desirable to provide a means for first fixing the angle of entry of the probe, and further a means of providing rotation of a probe whose entry angle has been locked.

In accordance with the present invention, there is provided a device for directing a probe, comprising:
 a) a plate having a proximal face, a distal face adapted to conform to the patient's back, and a throughhole extending from the proximal face to the distal face, wherein at least a portion of the throughhole forms a substantially spherical recess, and
 b) a substantially spherical bearing disposed in the substantially spherical recess and adapted to received a probe.

This device allows the clinician to precisely orient the entry angle of the probe in the x, y and z planes. In the event the clinician decides the initial entry angle of the probe was incorrect, the device also allows the clinician to precisely change the entry angle of the probe in the x, y and z planes.

In some embodiments, it may be desirable that the device provide not only angular adjustment, but also X-Y adjustment of the entry point of the probe. For example, the clincian may decide that the entry point of the probe needs to be higher or lower, or to the left or to the right, etc., to create the desired trajectory through, for example, the pedicle. In some embodiments, the device is provided translational change capability. In some embodiments, the device comprises a conventional X-Y stage, preferably incorporated into the anchor. In other embodiments, a first sliding plate on a second plate is used.

In preferred embodiments, the anchor also allows the clinician to retain the freedom to rotate the probe after the entry angle has been locked.

Figure 14:
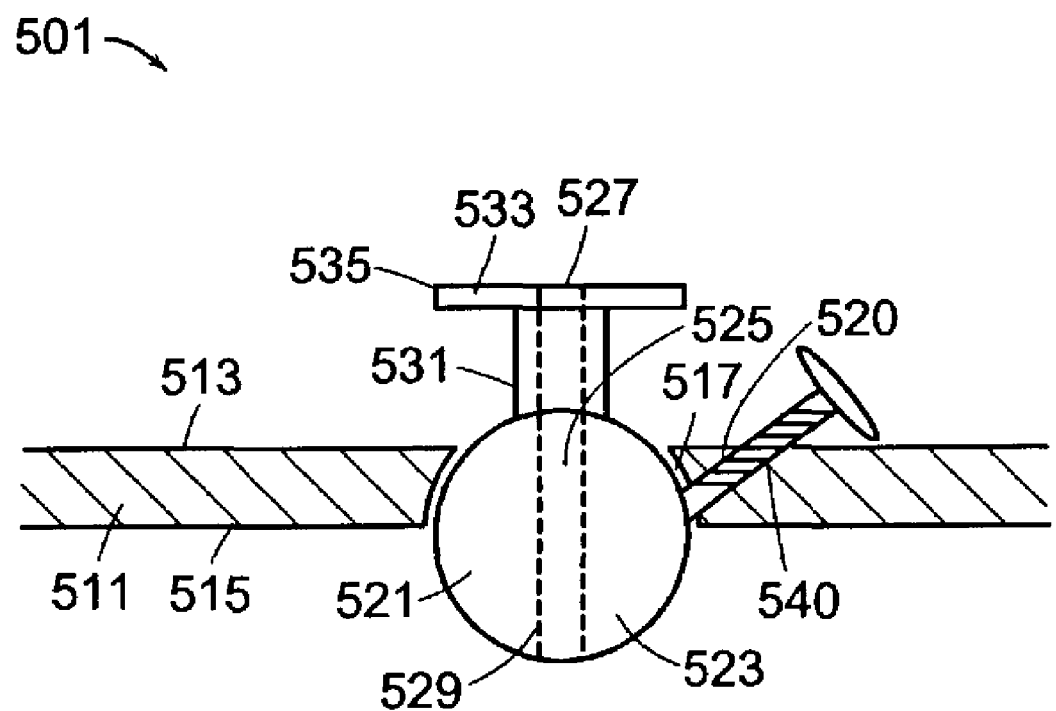
FIG. 14 discloses a cross-sectional view of an globe-type anchor of the present invention.

Now referring to FIG. 14, in preferred embodiments, there is provided a device 501 for directing a probe, comprising:
 a) a plate 511 comprising:
  i) a proximal face 513,
  ii) a distal face 515 adapted to conform to the patient's back,
  iii) a first throughhole 517 extending from the proximal face to the distal face, wherein at least a portion of the throughhole forms a portion of a spherical recess, and
  iv) a second throughhole 520 extending from the proximal face to the substantially spherical recess,
 b) a bearing 521 comprising:
  i) a substantially spherical portion 523 disposed in the substantially spherical recess,
  ii) an annulus 531 formed upon the proximal portion of the bearing and further having a proximal end portion 533 and a laterally extending proximal lip 535,
  iii) a third throughhole 525 extending from the distal portion of the substantially spherical portion to the proximal portion of the annulus, defining a proximal opening 527 and a distal 529 opening, and
 c) a lock screw 540 adapted to be inserted into the second throughhole of the plate and fix the orientation of the bearing.

In use, the clinician first fixes the plate the patients' back by means of an adhesive, uses the graduations disposed on the globe surface to fix the entry angle of the probe, inserts the locking screw into the locking hole to lock the orientation of the globe, and inserts the probe through the first throughhole so that the probe enters the patient at the desired vector. In some embodiments, the clinician rotates the housing about the annulus 531 in order to rotate the probe.

In other embodiments, the device for fixing the probe entry angle comprises:
 a) a hollow hemispherical body having an outer rim and a passage at its apex, and
 b) a mounting plate having a distal side having adhesive thereon, a proximal side having a sticky coating (such as silicon) thereon, a centered throughhole, and graphic concentric rings that report the change in angle of a probe passing through the passage and the throughhole in response to movement of the hollow hemispherical body about the mounting plate.

Figure 5:
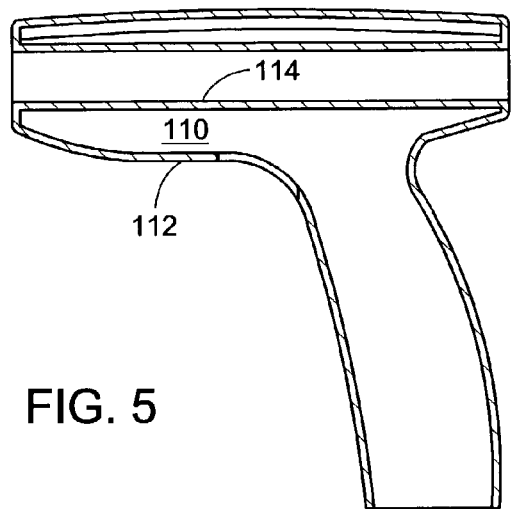
FIG. 5 discloses a cross-section of a housing of the present invention having a second passage forming a junction with the first passage.

Referring to FIG. 5, in some embodiments, the housing further comprises a second passage 110 in connection with the first passage. Preferably, this second passage is adapted to provide an access portal to place the advancement mechanism in connection with the outer surface of the probe. In some embodiments, the second passage forms a third opening 112 on a lateral side of the base portion, extends into the base, and meets the first passage at a junction 114. Preferably, this junction is located on the proximal/distal portion of the housing.

Figure 6:
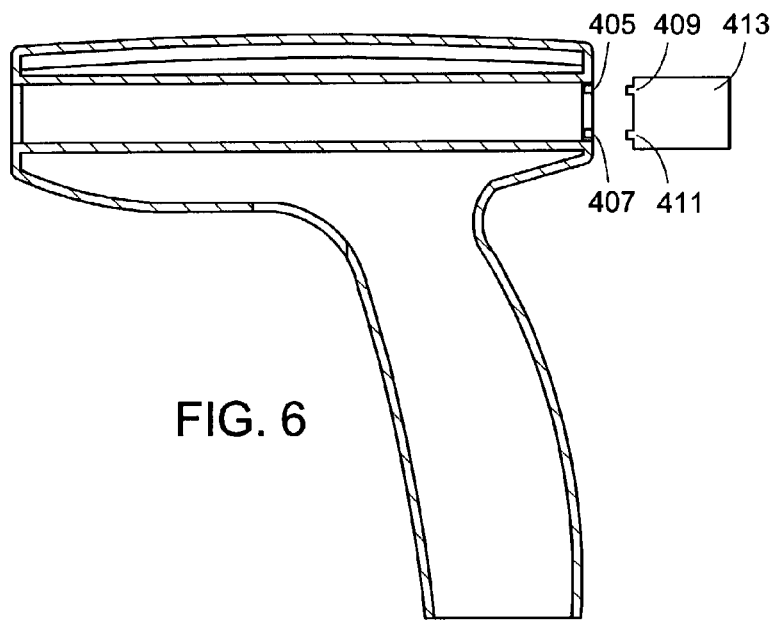
FIG. 6 discloses an exploded cross-section of a housing and an advancement means of the present invention.

Now referring to FIG. 6, in some embodiments, the housing further comprises a flange or port upon which the advancement mechanism can be mounted. In FIG. 4, two ports 405, 407 are disclosed that are adapted to mate with corresponding flanges 409,411 disposed upon advancement mechanism 413. In some embodiments, the flanges are located on the proximal face of the housing. In other, the flanges are located on the upper or lower faces of the housing.

In some embodiments, the housing further comprises a distally-disposed probe stop. Now referring to FIG. 4, the probe stop 751 comprises a semi-flexible flange 753 having a first end 755 attached to the housing, a second end 757, a proximal face 758, a distal face 759 and a proximal-distal throughhole 760. Preferably, the throughhole is disposed over the proximal opening of the housing so that a probe can pass through each. The throughhole has a teardrop shape having an upper end 761 sized to allow passage of the probe and a narrowed lower end 763 sized to stop passage of the probe.

In a non-actuated state, the stop is disposed essentially normal to the probe axis and the probe rests in the narrow lower end of the throughhole. In this state, the friction between the lower end of the teardrop and the probe is such that the probe can not advance. When the clinician pushes the proximal face of the stop in the distal direction, the upper end of the flange bends distally. This bending pushes the upper end of the throughhole downward so that widened portion of the teardrop now surrounds the probe. Because the widened portion of the teardrop allows passage of the probe, the probe may now be advanced through the first passage.

Preferably, the probe of the present invention has a shape suitable for penetration of tissue, preferably hard tissue, more preferably cortical bone.

In some embodiments, the probe has a length L and an outer surface having a width W, wherein the length is at least five times greater than the width. In this condition, the probe can suitably enter a vertebral body via a pedicle and still reach at least the midpoint of the vertebral body. In preferred embodiments, the length of the probe is between 50 and 100 mm, and the width of the probe is between 1 and 3 mm, preferably 1 mm and 2 mm.

The functional element is selected from the group consisting of any element capable of aiding diagnosis, delivering energy, or delivering or removing a material from a location adjacent the element's location in the catheter, such as an opening in the catheter for delivery of a substance such as fluid or a solid, or for suction, a thermal energy delivery device (heat source), a cutting tool (which includes all similar operations, such as puncturing), a sensor for measurement of a function (such as electrical resistance, temperature or mechanical strength), a sensor for visualization, a guidance tool for allowing passage of other devices (such as a catheter, wire or sutre), or a functional element having a combination of these elements.

In some embodiments, the functional element may include a portion of the probe. For example, in the case of an electrically conductive probe having insulated portion and a non-insulated portion in electrical connection with a power supply, the uninsulated portion of the probe could be considered to be an electrode, and so would be considered to be a functional element.

In some embodiments, the functional element delivers antibiotics.

Preferably, the functional element is a thermal energy delivery device. These devices are particularly suited for denervating intraosseous nerves in general, and the basivertebral nerve in particular. More preferably, the functional element is an active electrode capable of transmitting Rf energy. In some embodiments, the functional element is a bipolar electrode having an active electrode and a return electrode. In some embodiments, two probes are used to form a bipolar electrode, wherein one probe has an active electrode and the second probe has the return electrode.

In some embodiments, the outer surface of the probe has teeth extending outwardly from the outer surface.

Therefore, in accordance with the present invention, there is provided a device for therapeutically treating bone, comprising:

a) a housing having a base portion having a distal face, and a first passage opening upon the distal face and forming a longitudinal axis, b) a probe adapted to advance through the first passage along the longitudinal axis, the probe having a functional element thereon and an outside surface having outwardly extending teeth, and c) an advancement mechanism adapted to advance the probe through the first passage.

Preferably, these teeth are shaped for engaging with complimentary teeth of the advancement mechanism. Preferably, these teeth are disposed substantially on the proximal half of the probe. Preferably, the teeth have a length of between 10% and 50% of the width of the probe. In some embodiments, the teeth are disposed proximal to the electrode. In this condition, a probe having a distal electrode is conveniently advanced within the tissue by engagement of the proximal teeth with the advancement mechanism associated with the housing. In some embodiments, the teeth have a proximal face and a distal face, wherein the proximal face is oriented at an angle to the probe and the distal face is essentially normal to the probe. In some embodiments, the plurality teeth are provided in a substantially fixed increment of separation. In other embodiments, the plurality teeth are provided in a first large increment of separation (in order to advance quickly to the target area), and a second smaller increment of separation (to provide accuracy when adjacent the target area).

In some embodiments, the outer surface of the probe has no teeth and so is substantially smooth. Some clinicians may prefer a toothless probe due to a concern that the teeth may cause unwanted damage to the tissue over which they pass. In embodiments in which the probe is substantially toothless, the means for advancing the probe also is substantially toothless, and typically has a friction means for advancing the probe. A toothless probe may be advanced at variable increments determined at the time of the procedure.

A metering device may also be provided with either a toothless or toothed probe so that the clinician may meter in the amount of advance desired. In some embodiments, the metering device may provide a first large increment of separation (in order to advance quickly to the target area), and a second smaller increment of separation (to provide accuracy when adjacent the target area).

Therefore, in accordance with the present invention, there is provided a method of positioning a probe within hard tissue, comprising the steps of:

a) positioning a probe comprising a functional element at a first location in the hard tissue, b) selecting a first predetermined length of advance of the probe, advancing the probe the first predetermined length to a second location in the tissue.

In some embodiments, the probe is hollow, thereby defining an annulus and a bore. When the probe is hollow, a lead wire can be conveniently passed through the bore to electrically connect an electrode disposed on the annulus with a power supply.

In some embodiments, it is useful to be able to offset the functional element from the longitudinal axis of the advance. Such an offset provides useful directionality to the device.

In some embodiments, this offset is achieved by providing the probe with an articulating arm having the functional element to be offset. The articulating arm can be deployed after the probe is fully distally advanced.

In other embodiments, the probe can be housed within a cannula having a curved inner surface opening onto a lateral opening in the distal portion of the cannula. In this embodiment, both the probe and cannula are distally advanced through the first passage and into the tissue, and then the probe is further advanced through the lateral opening of the cannula.

In other embodiments, the offset may be achieved by pull wires attached to a distal portion of the probe. The pull wires can be deployed after the probe is fully distally advanced.

In some embodiments in which an articulated probe is used in conjunction with a cannula, the cannula can be used as a protective sheath. For example, when an articulated probe having a forward-pointing arm is deployed, the point of the arm moves in an arc in the proximal direction. If this arm is somehow mis-deployed, the cannula from which is advanced can now be advanced over the articulation to redirect the arm distally and thereby close the articulation.

Figure 16:
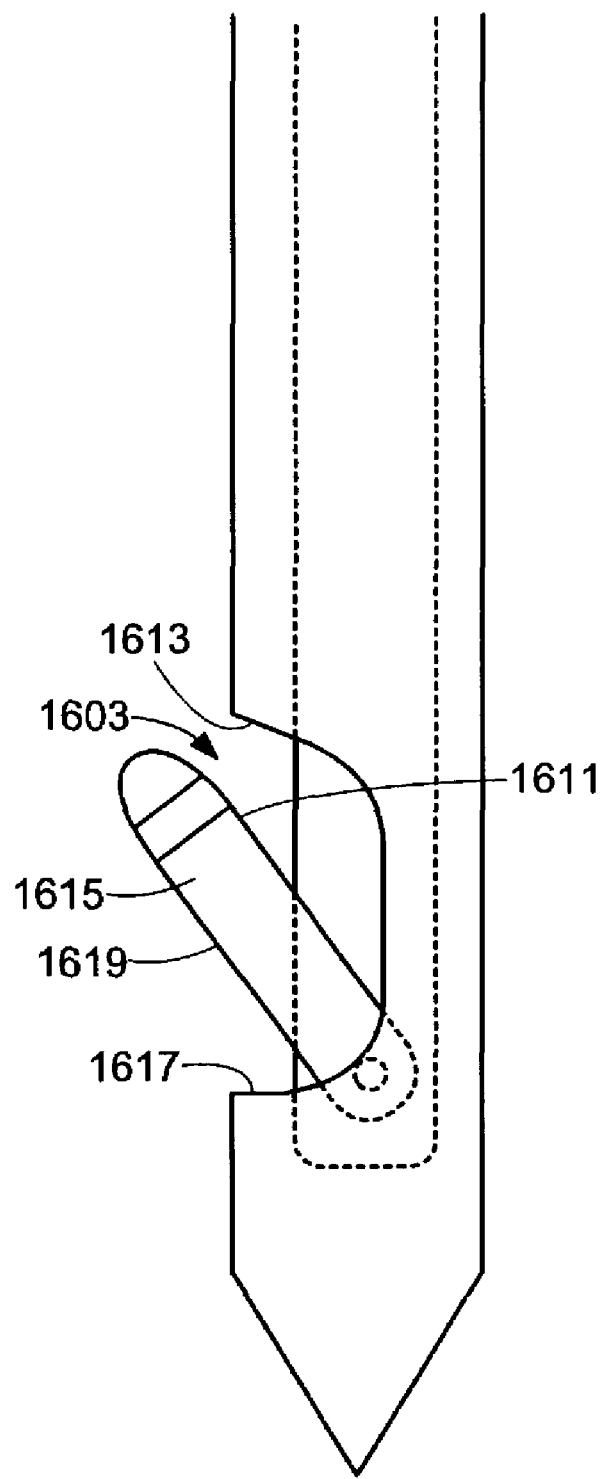
FIG. 16 discloses probe of the present invention housing in a protective sheath.
Figure 17:
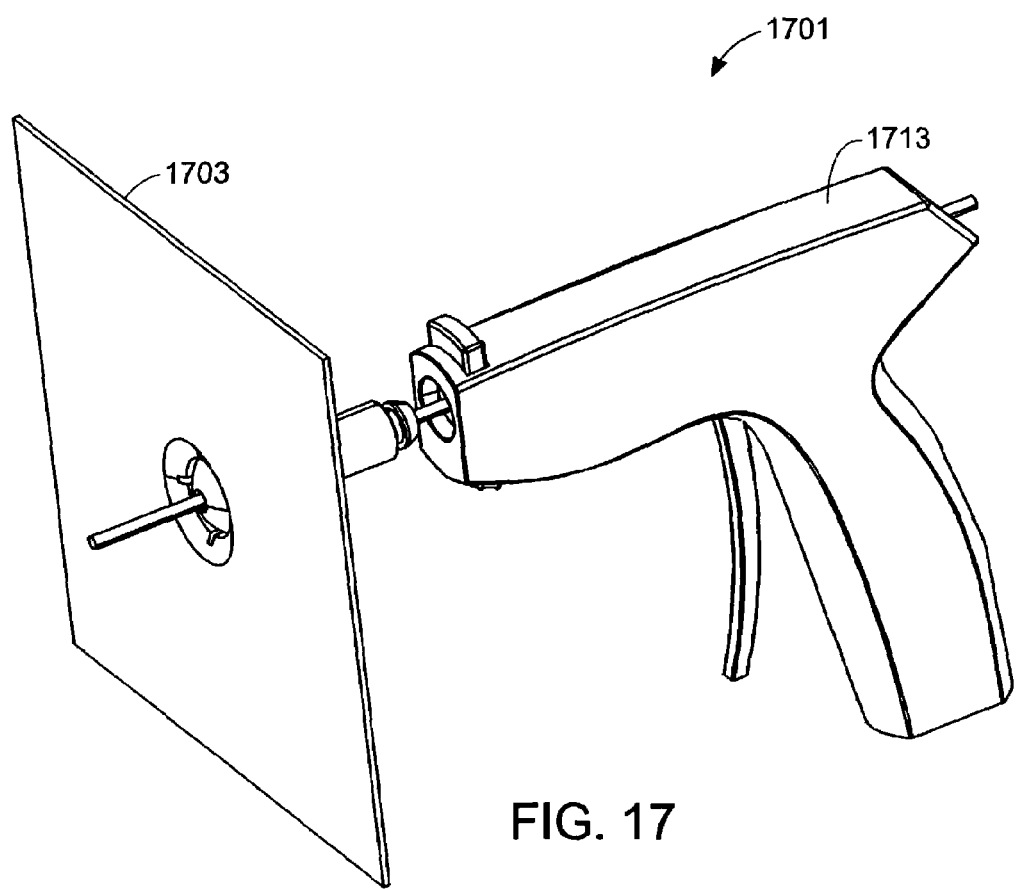
FIG. 17 discloses a perspective view of a preferred embodiment of the present invention.
Figure 18:
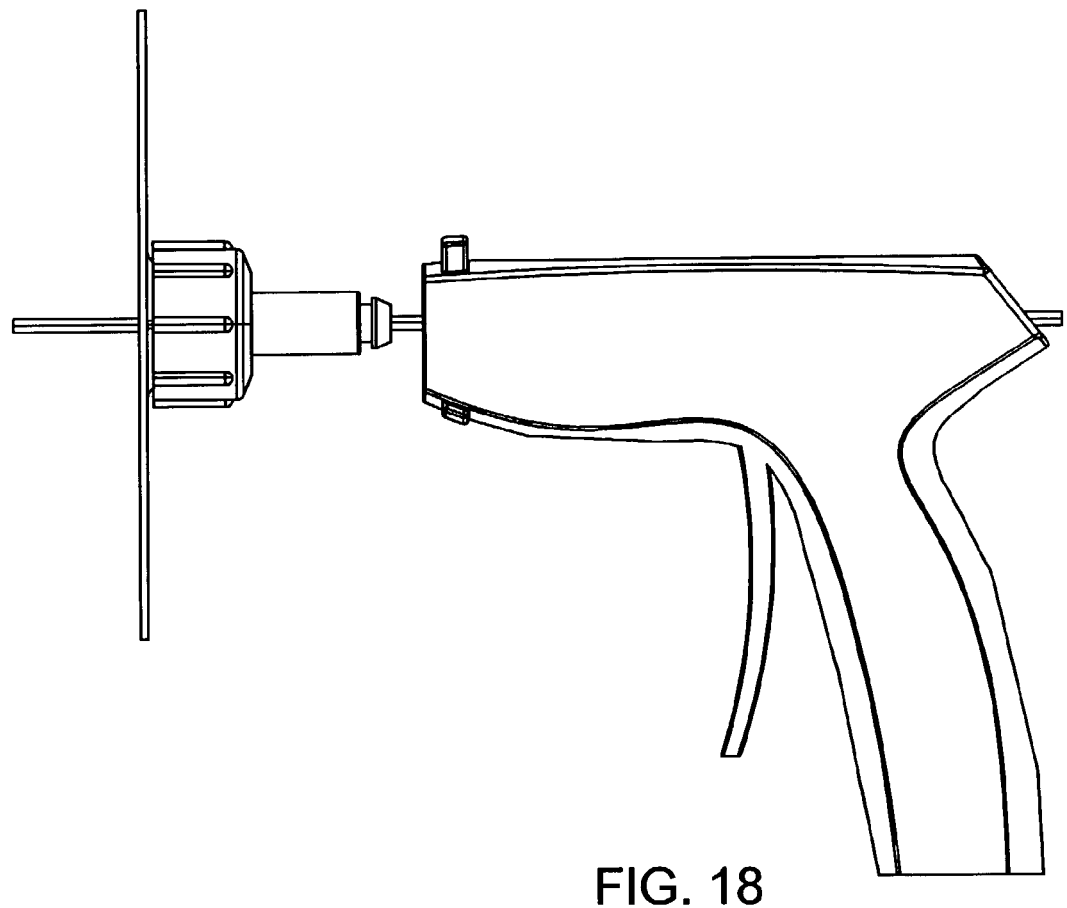
FIG. 18 discloses a side view of a preferred embodiment of the present invention.

Now referring to FIG. 16, in other sheath embodiments, the cannula comprises a hollow tube having a pointed end and a lateral opening 1603 through which the pivotable probe may pass. After the pivotable probe is deployed (so that its inner edge 1611 extends outside the tube, the clinician can push down on the tube so that the proximal edge 1613 of the lateral opening pushes against the inner edge of the pivotable probe, thereby causing further pivoting of the pivotable arm 1615 and bringing the pivotable arm to its fully deployed state. After treatment, this fully deployed probe can be retracted by pulling on the tube, thereby causing the distal edge 1617 of the lateral opening to push against the outer edge 1619 of the pivotable probe and forcing the pivotable probe back into the fixed probe.

In some embodiments, the distal end of the probe comprises a tip which has sufficient sharpness to pierce bone, preferably cortical bone. Preferably, the tip of sufficient sharpness forms an angle α of between about 15 and 30 degrees.

Therefore, in accordance with the present invention, there is provided a device for therapeutically treating bone, comprising:

a) a housing having a base portion having a distal face, and a first passage opening upon the distal face and forming a longitudinal axis, b) a probe having a electrode functional element, the probe adapted to advance through the first passage along the longitudinal axis, the probe having a distal end portion shaped to penetrate bone, and c) an advancement mechanism adapted to advance the probe through the first passage.

In some embodiments, the outer surface of the probe is graduated with a plurality of graduations 341 so that the depth of penetration of the probe into the tissue can be readily confirmed.

Therefore, in accordance with the present invention, there is provided a device for therapeutically treating bone, comprising:

a) a housing having a base portion having a distal face, and a first passage opening upon the distal face and forming a longitudinal axis, b) a probe adapted to advance through the first passage along the longitudinal axis, the probe having an outer surface having graduations thereon and a functional element thereon, and c) an advancement mechanism adapted to advance the probe through the first passage.

Figure 7:
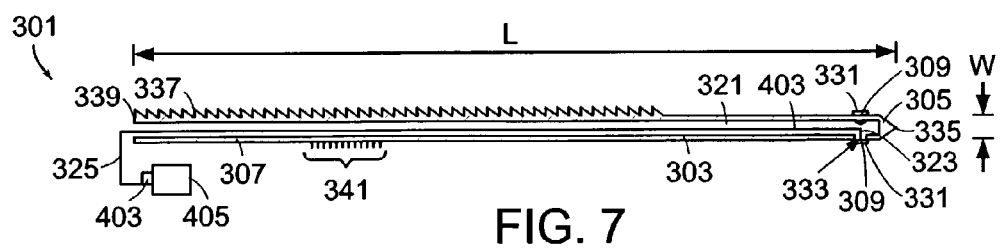
FIG. 7 discloses a cross-section of a preferred probe of the present invention.

Referring now to FIG. 7, probe 301 comprises a shaft 303 having a longitudinal axis B and a distal end portion 305 and a proximal end portion 307. Disposed near the distal end portion of the probe is first electrode 309 having a first face 331 and a connection face 333. The probe is designed so that the connection face of the first electrode is placed in electrical connection with a first lead 403 of the power supply 405. In this particular embodiment, the shaft has a longitudinal bore 311 running from the proximal end portion up to at least the first electrode. Disposed within the bore is a wire 321 electrically connected at its first end 323 to the first electrode and having a second end 325 adapted to be electrically connected to a first lead of a power-supply.

The probe 301 further comprises a distal tip 335 having sufficient sharpness to pierce bone and a plurality of teeth 337 formed along the longitude of and extending from the outer surface 339 of the shaft.

Figure 19:
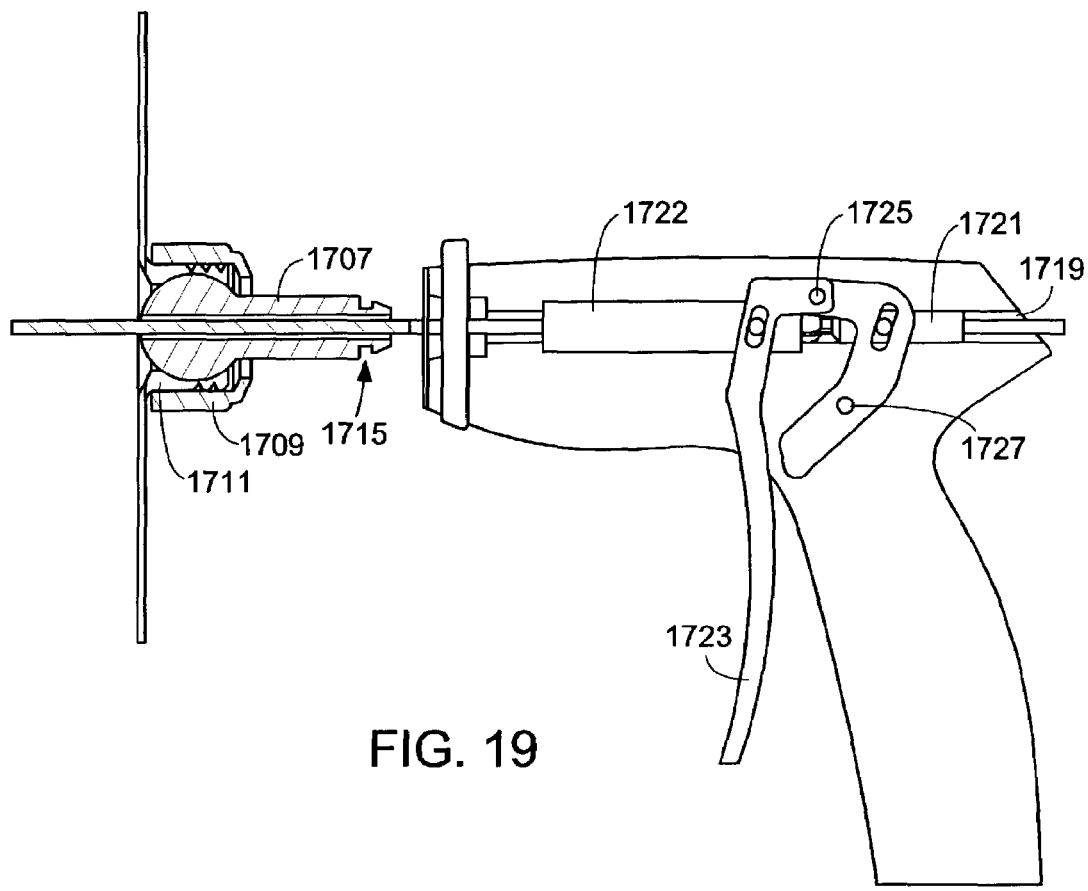
FIG. 19 discloses a cross-sectional view of a preferred embodiment of the present invention.
Figure 20:
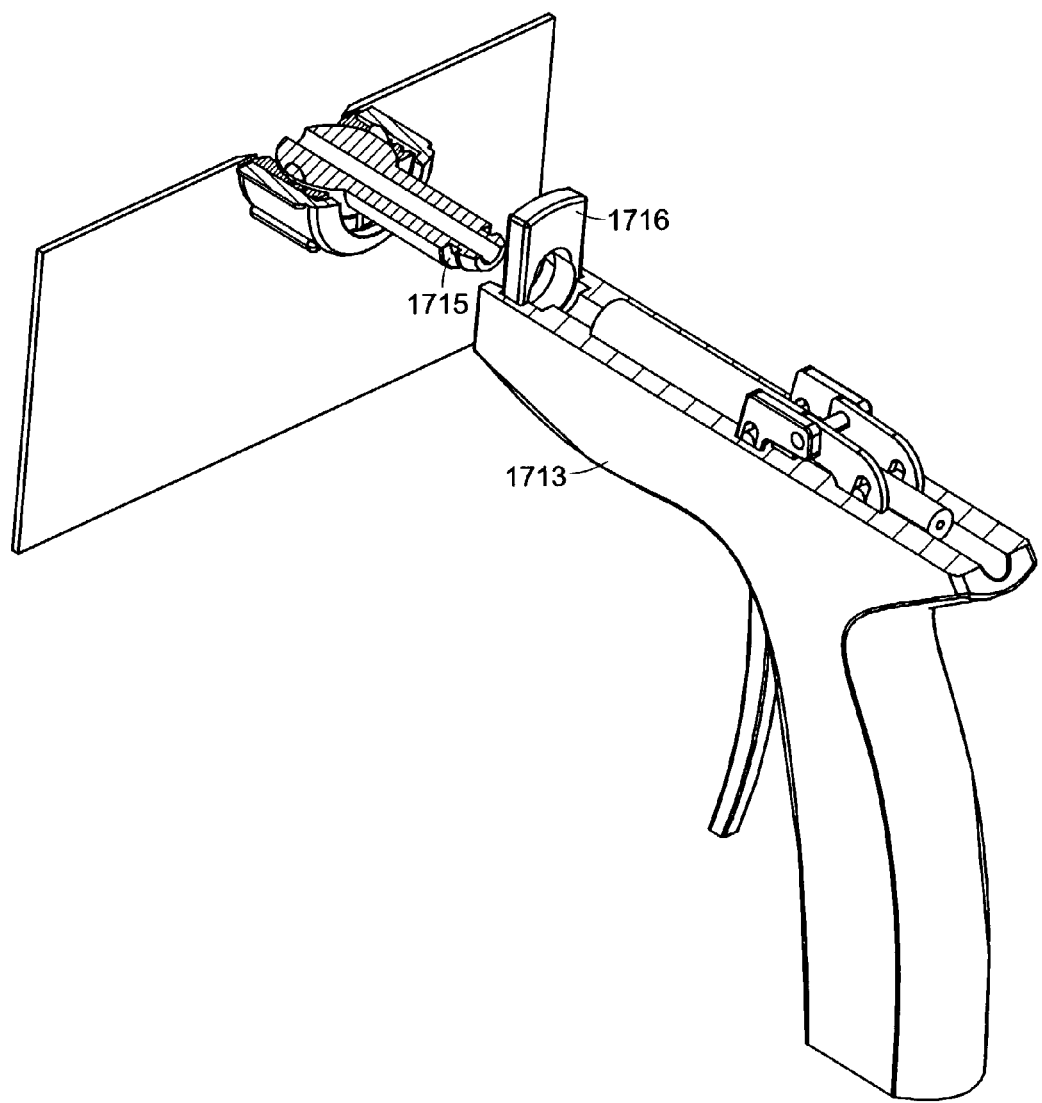
FIG. 20 discloses a perspective view of a preferred embodiment of the present invention, wherein the upper portions of the attachment and the housing components are removed.
Figure 21:
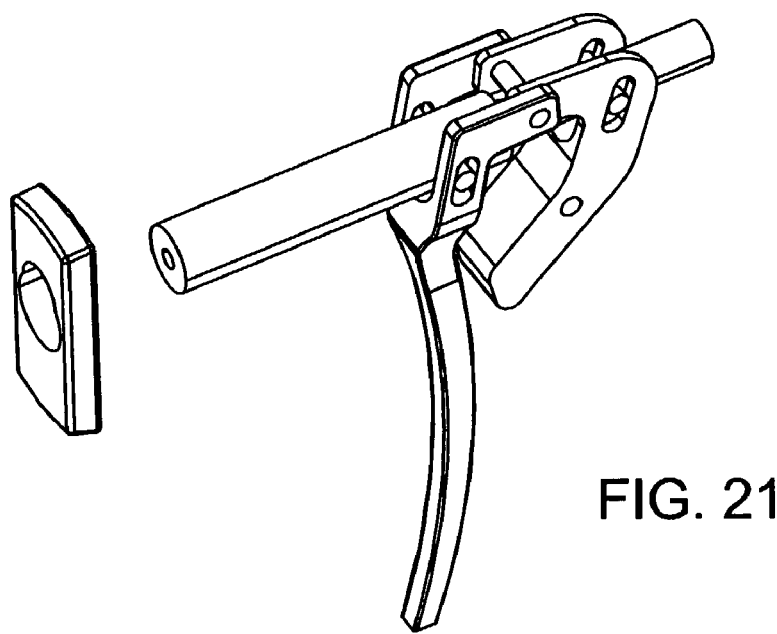
FIGS. 21 and 22 disclose perspective and side views of the advancement mechanism of the device of FIG. 20.
Figure 22:
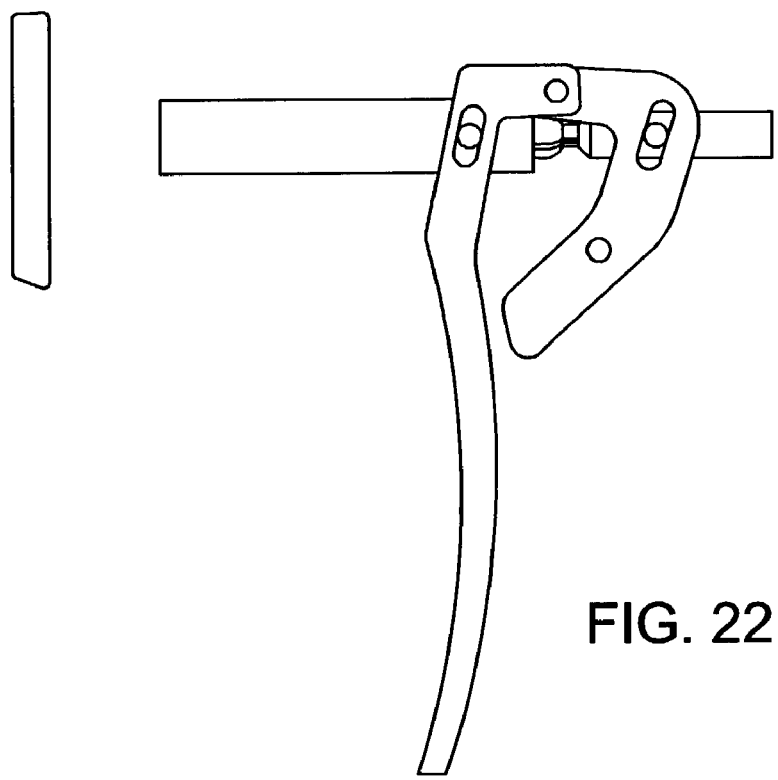

Any conventional means for incrementally advancing a probe within a passage may be used as the advancement mechanism. In some embodiments, a ratchet and pawl mechanism is selected. In others, the advancement mechanism comprises a rack and pinion mechanism (such as a crank). In others, the advancement mechanism comprises a friction-based mechanism, such as those in FIGS. 4, 19 and 22, and a leaf spring. In others, the advancement mechanism comprises a tension band wound with a pulley that is wound in.

In some preferred embodiments in which a tension band mechanism is employed. the mechanism comprises a housing having a throughbore therethrough and a take-up spool mounted thereon. The distal end of the tension band is fixed to the take-up spool, while its proximal end is attached (e.g., by a hook) to a proximal end of the probe. Lastly, the distal end portion of the probe is positioned within the throughbore of the housing distal end When the spool is turned to take up the band, the probe advances distally through the throughbore. Because the probe advances without the use of a ratchet, the probe can be toothless. In preferred embodiments, the take up ban may have graduations to indicate the extent of advance.

In some leaf spring mechanisms, the mechanism is spring loaded to lock the probe and has a slanted thin blade that prevents sliding of the tube through the blade.

In some embodiments, the advancement mechanism is mounted within the housing, thereby providing a compact device. In some embodiments, the advancement mechanism is disposed upon a lateral side of the housing, and engages the probe through a second passage within the housing. In some embodiments, the advancement mechanism is disposed near the proximal opening of the first passage the housing, and engages the probe at a location proximal to the proximal opening of the first passage in the housing.

In some preferred embodiments, a ratchet and pawl assembly is used as the advancement mechanism. Any conventional ratchet and pawl assembly may be used. In some embodiments, the ratchet and pawl mechanism as shown in FIG. 1 is used. In other embodiments, a multiple ratchet and pawl mechanism comprising at least two pawls is used in order to provide fine incremental advance of the probe. In some embodiments, reverse ratchet is used in order to allow the probe to be advanced either distally or proximally. In other embodiments, a frictional ratchet is used.

Figure 8:
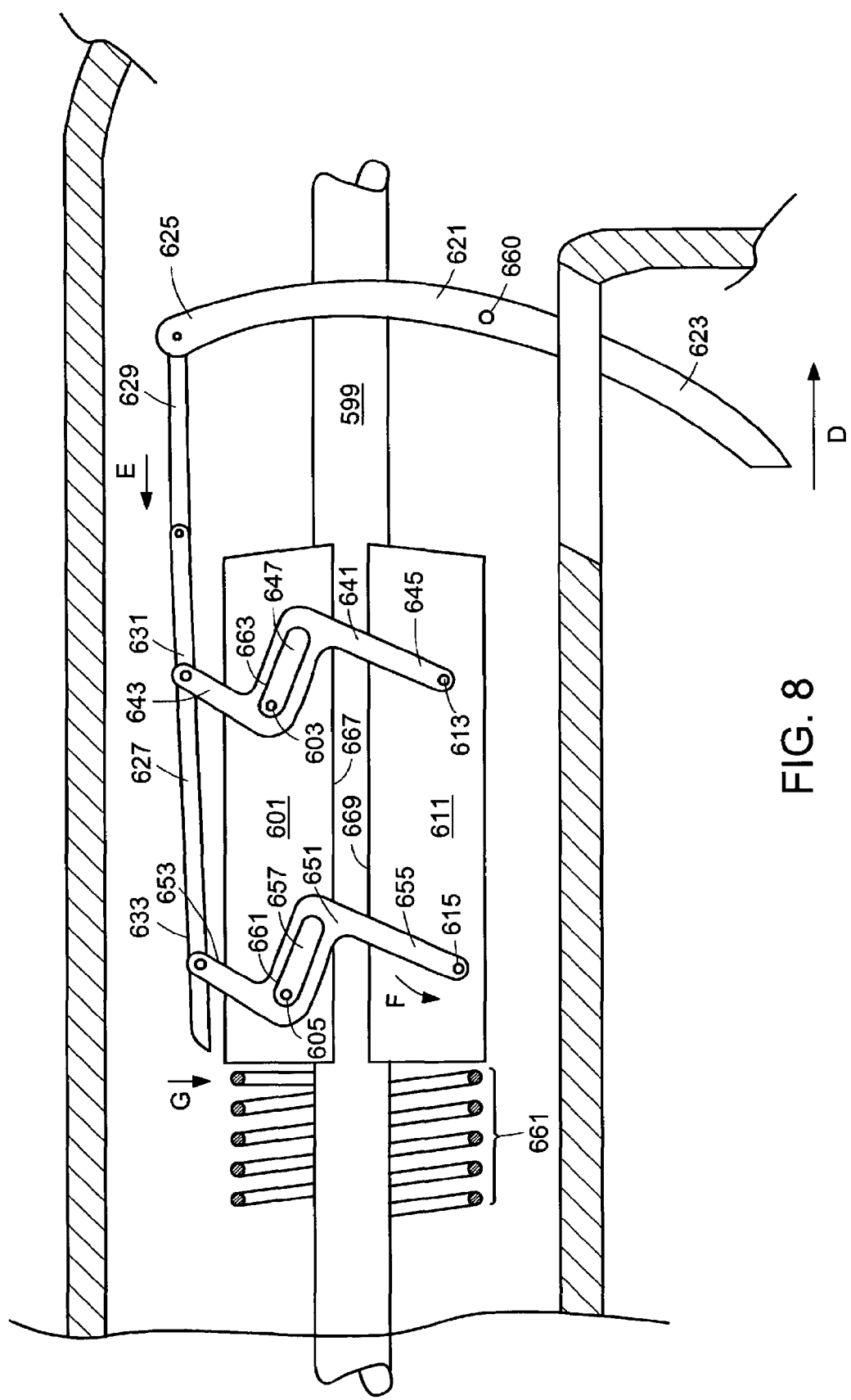
FIG. 8 discloses a cross sectional view of another embodiment of the present invention FIG. 9 discloses a side view of a crank of the present invention.

Now referring to FIG. 8, there is provided a preferred advancement mechanism comprising:
a) an upper block 601 positioned above the first passage 599 and having proximal 603 and distal 605 pins extending in the same direction,
b) a lower block 611 positioned below the first passage and having proximal 613 and distal 615 pins extending in the same direction,
c) a lever 621 having a proximal end portion 623 pivotally attached to the base and a distal end portion 625,
d) bar 627 disposed above the upper block and having a proximal portion 629 pivotally attached to the distal end portion of the lever, an intermediate portion 631, and a distal portion 633,
e) proximal link 641 having an upper end 643, a lower end 645, and a through hole 647 located adjacent the upper block and extending between the upper and lower ends 643 and 645, the upper end being pivotally attached to the intermediate portion of the bar, and the lower end being pivotally attached to the proximal pin of the lower block,
f) distal link 651 having an upper end 653, a lower end 655, and a through hole 657 located adjacent the upper block and extending between the upper and lower ends 653 and 655, the upper end being pivotally attached to the distal portion of the bar, and the lower end being pivotally attached to the distal pin of the lower block,
g) bias means 661 positioned for urging the distal ends of the blocks proximally.

In some embodiments, each of the blocks is designed to float parallel to the axis of probe advancement. This may be accomplished by providing either a) a dovetail groove on the outer surface of each block, or b) a straight groove on a side of each block, and providing complimentary rails on the housing that mate with the corresponding grooves. In other embodiments, the groove and rails are reversed.

In some embodiments, a rubber O-ring is provided around the passage in a location distal of bias means 661 to provide a level of friction upon the probe that allows the probe to advance distally when the lever is pulled, but keeps the probe in place when the lever is retracted; a compression spring is provided between the lower block 611 and the housing in order to allow the lower block to float; and the joints formed by pins 603,605 and links 641,651 are designed to be low friction.

Typically, the upper block is held within the housing substantially means of its linkage with the lower block. The lower block may be slidably received upon the housing by conventional means. For example, the lower surface of the lower block may possess a longitudinal dovetail groove shaped for slidable reception within in a corresponding longitudinal dovetail projection located on the housing. Alternatively, a side surface of the lower block may possess a longitudinal straight groove shaped for slidable reception in a corresponding longitudinal straight projection located on the housing.

In use, when the lever is pulled in the direction signified by arrow D, the lever pivots about pin 660, and its distal end pushes the bar in a distal direction (signified by arrow E). Movement of the bar in the distal direction E causes the lower ends of the associated links to move counterclockwise (signified by arrow F) as they pivot about pins 613 and 615. Movement of this link in this direction causes the upper surfaces 661,663 of the links' through-holes to bear against the associated fixed pins 603,605 located on the upper block. The bearing of surface 661,665 against pins 603,605 pushes the upper block in the direction of the first passage (signified by arrow G). When the upper block is pushed sufficiently downward, its lower surface 667 engages the upper surface of the probe (not shown) while the upper surface 669 of the lower block engages the lower surface of the probe (not shown). Upon engagement, the blocks, the links and probe will move as one in the distal direction E. Further movement of the lever in the D direction causes further movement of the probe in the distal direction E. When a single actuation is complete, the clinician releases the grip, thereby allowing the lever to be urged back to its original position by a spring (not shown), and allowing expansion spring 661 to pushes the blocks back to their original positions. Proximally positioned tab is designed so that pushing on its upper end will release the probe.

In another embodiment, the lower block is fixed to the housing while the top block remains axially moveable. In a first step, the initial pull causes each block to contact the probe, thereby providing upper and lower contact surfaces wherein the upper contact surface has a higher friction coefficient than the lower contact surface. Since the lower contact surface has a lower friction coefficient, the probe will slide along the upper surface of the lower block.

This embodiment is useful because the advancement mechanism does not require that the probe have teeth for engagement therewith, and the advance may be carried out in variable increments.

Therefore, in accordance with the present invention, there is provided a method of providing therapy to a tissue, comprising the steps of:
a) providing a device for therapeutically treating bone, comprising:
    i) a housing having having a distal face, and a first passage opening upon the distal face and forming a longitudinal axis,
    ii) a probe adapted to advance through the first passage along the longitudinal axis, the probe having a functional element thereon, and
    iii) an advancement mechanism adapted to advance the probe through the first passage,
b) inserting the probe into a bone,
c) actuating the advancement mechanism to advance the probe in the vertebral body, and
d) activating the functional element to therapeutically treat the bone.

Figure 9:
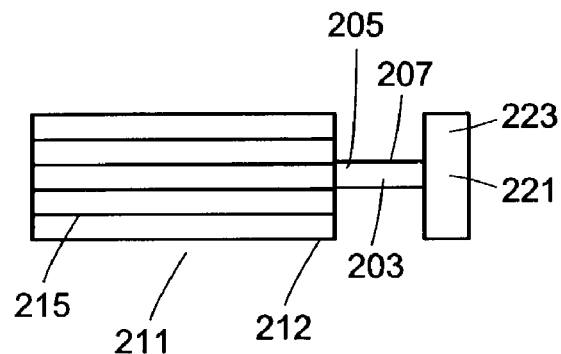

In some embodiments, and now referring to FIG. 9, the advancement mechanism comprises a crank. Preferably, the crank 201 comprises:
i) a rod 203 rotatably received within a passage the housing, and a having a distal end 205 and a proximal end 207 forming a longitudinal axis C,
ii) a rotatable cylinder 211 having a proximal end 212 mounted to the distal end of the rod, and comprising an outer circumference having ridges 215 extending therefrom in the direction of the longitudinal axis C, and
iii) a knob 221 mounted to the proximal end of the rod, and having at least one wing 223 extending therefrom.

Figure 10A:
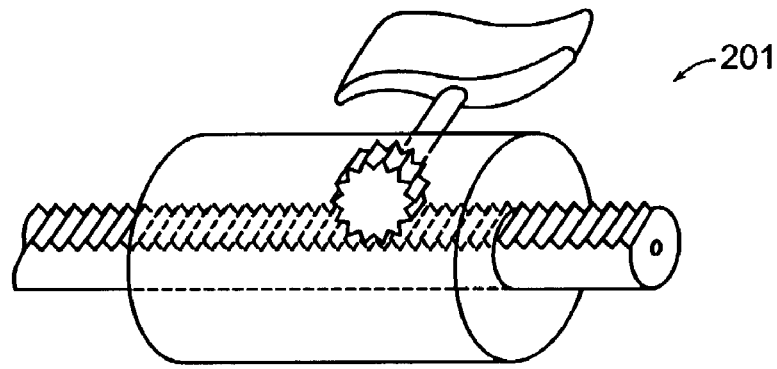
FIGS. 10a-b disclose perspective and cross-sectional views of another embodiment of the present invention wherein the advancement mechanism comprises a crank.
Figure 10B:
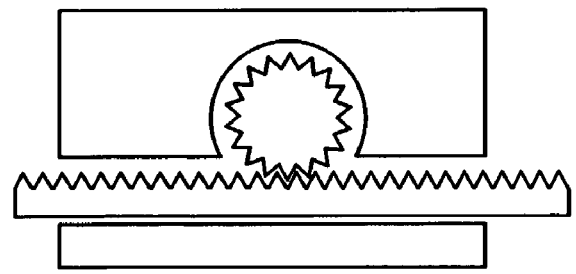

In preferred embodiments, as in FIGS. 10a and 10b, the crank is oriented with respect to the probe so that the cylinder's ridges engage the probe's teeth. Mechanical advantage of the crank may be increased by increasing the length of the at least one wing.

In some embodiments, the crank is provided with a one-way clutch to prevent the crank from reversing direction until its disengagement from the teeth of the probe.

Figure 11:
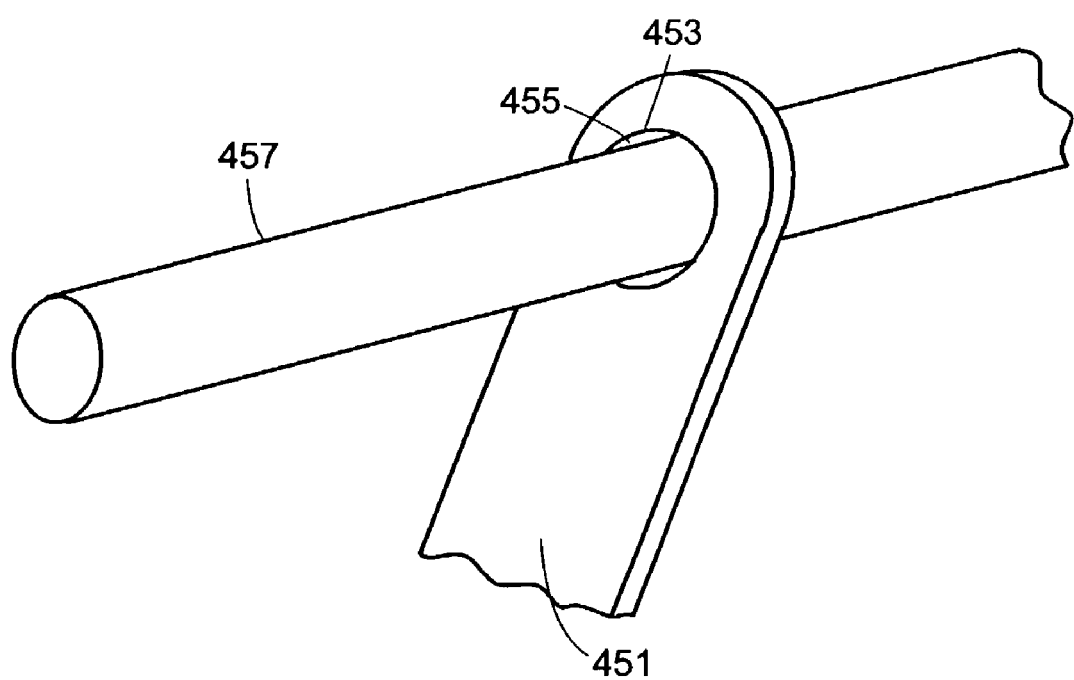
FIG. 11 disclose perspective and cross-sectional views of another embodiment of the present invention wherein the advancement mechanism comprises a smooth engagement means.

Now referring to FIG. 11, in some embodiments, the toothed wheel may be replaced by a smooth flange 451 extending from the lever and having a throughhole 453 forming an inner surface 455 adapted to slidably receive the probe. In this condition, actuation of the lever causes the inner surface formed by the throughhole to frictionally contact the outer surface 457 of the probe. This friction allows the flange to advance the probe distally. In this embodiment, the probe does not need to have teeth.

Figure 15:
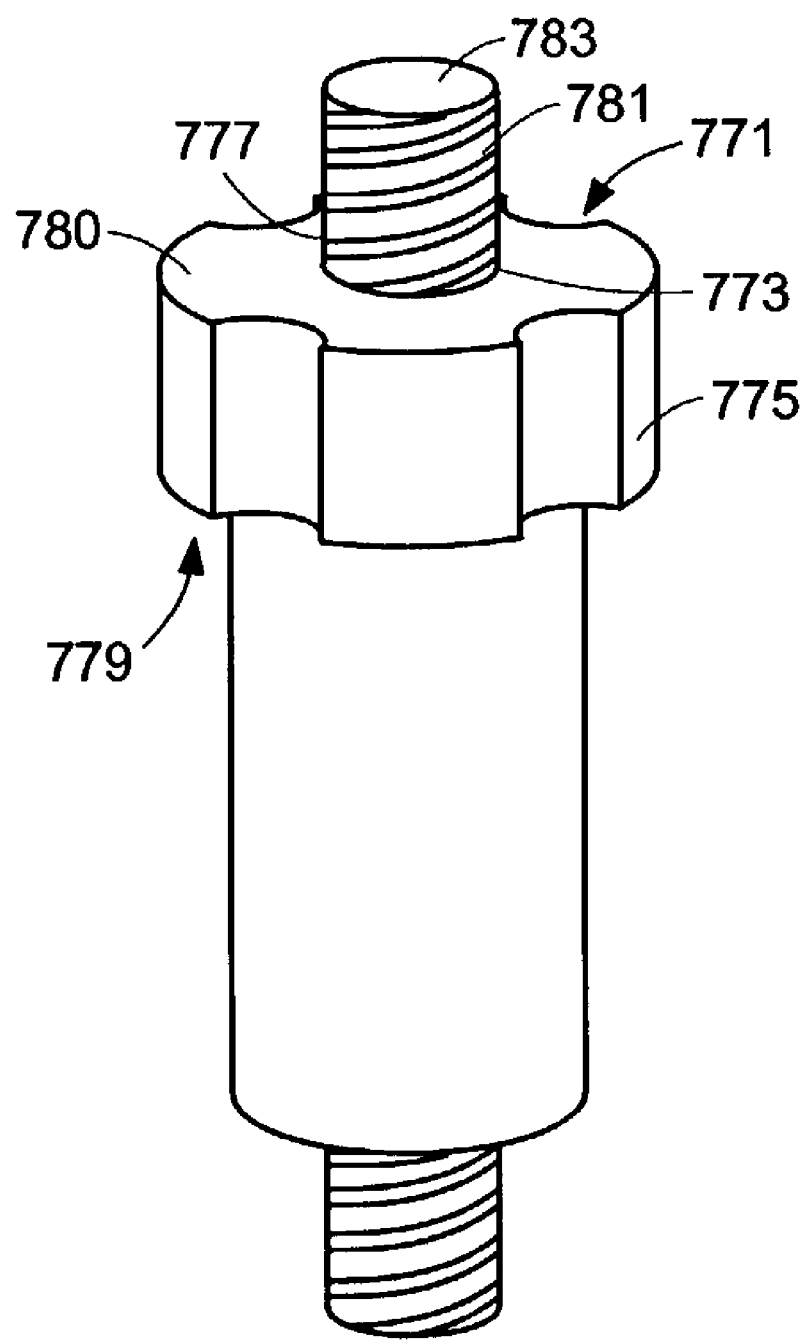
FIG. 15 discloses a side view of a threaded collar advancement mechanism of the present invention.

Now referring to FIG. 15, there is provided an embodiment of the present invention wherein the advancement mechanism comprises a threaded collar adapted to advance the probe by threaded engagement.

Therefore, in accordance with the present invention, there is provided a device for therapeutically treating bone, comprising:
a) a housing having a base portion having a distal face, and a first passage opening upon the distal face and forming a longitudinal axis,
b) a longitudinal element adapted to advance through the first passage along the longitudinal axis, the probe having a threaded outer surface, and
c) an advancement mechanism adapted to threadably advance the longitudinal element through the first passage.

In the embodiment shown in the FIG. 15, the threaded collar 771 has an annulus 773 defining an outer surface 775 and a threaded inner surface 777, a distal face 779 and a proximal face 780. The outer surface 781 of the probe 783 has a thread pattern corresponding to that of the threaded inner surface. The distal face of the threaded collar is disposed against the proximal face of the housing around the proximal opening. When the outer surface of the threaded collar is rotated in a clockwise direction, the mating threads push the probe distally)

The device of this embodiment is useful not only for threadably advancing probes having functional elements, it may also be useful in threadably advancing threaded fasteners, such as screws, such as pedicle screws.

In some embodiments, the advancement mechanism is designed to provide distal advance of the probe in increments of between 1 mm and 10 mm, preferably between 1 mm and 5 mm. These increments are particularly well suited for advancing a probe into a vertebral body. Increments below 1 mm may undesirably lengthen the procedure time, while increments above 10 mm may undesirably reduce the accuracy of the procedure.

In the some embodiments, the probe is advanced without rotation. When the probe is so advanced, there is little chance of it causing loose tissue (such as skin) from o wrapping around the probe. In some embodiments, the probe is advanced with rotation. When the probe is so advanced, the functional element can be directed by the rotation to face in a selected radial direction, thereby providing for additional targeting and accuracy.

In some embodiments, the advancement mechanism is designed to provide a mechanical advantage of at least 2:1, preferably at least 4:1. Typically, this is accomplished by providing an advancement mechanism having a lever.

In conventional procedures in which a probe is manually inserted, resisting forces within the target tissue may cause the probe to back out of the tissue. Accordingly, preferably, the advance mechanism of the present invention is further adapted to prevent the backout of the probe once is has been inserted into the target tissue. This feature is typically accomplished by providing friction between the advancement mechanism and the probe. For example, in the device of FIG. 11, the friction between the outer surface of the probe and the throughhole may be sufficient to prevent the backout of the inserted probe.

In some embodiments, a stylet and/or a cannula may be first inserted into the vertebral body prior to insertion of the probe. In general, the stylet is used by the clinician to puncture hard tissue (such as the cortical shell of a vertebral body), while the cannula may provide a passageway for the probe or a means of steering the probe.

Now referring to FIG. 12, stylet 471 comprises a shaft 473 having a longitudinal axis A, a proximal end 475 and distal end portion 477. Disposed at the distal end of the shaft is a tip 479 adapted for boring or drilling through bone. In some embodiments, the outer diameter $D_O$ of the shaft is adapted to be received within the inner diameter $D_C$ of the cannula (FIG. 13).

In some embodiments, a stylet may be used (without a cannula) to penetrate both the hard cortical shell and inner cancellous region of the vertebral body and form a passage for the probe. Once the stylet forms the passageway, the stylet is removed and the probe is advanced therein.

Now referring to FIG. 13, cannula 481 comprises a shaft 483 having a longitudinal bore 485 therein defining an inner diameter $D_C$, a proximal opening 487 and a distal opening 489. The cannula provides a working portal for the probe. In some embodiments, the distal opening of the bore opens laterally to provide a means of steering the probe off the longitudinal axis of the cannula. Rotation of this distal opening provides the clinician with the ability to steer the probe in a 360 degree direction.

In some embodiments, a cannula may be used (without a stylet) simply to penetrate the hard cortical shell of the vertebral body. Once the cannula has entered the vertebral body, the probe is advanced therein.

In some embodiments, the cannula and the stylet are used together as a "cannulated needle". In these embodiments, access to the vertebral body is gained by first placing the stylet in the cannula to produce the cannulated needle, piercing the skin with the cannulated needle, and advancing the cannulated needle so that the stylet tip reaches the cancellous portion of the vertebral body, and then withdrawing the stylet. This procedure produces a cannula whose distal opening conveniently located to provide access for a probe of the present invention to an intraosseous nerve (preferably, the basivertebral nerve.

In some embodiments having a cannula, it may be helpful to first fix the orientation of the cannula against the patient's skin.

Therefore, in accordance with the present invention, there is provided a device for therapeutically treating bone, comprising:
a) a housing having a base portion having a distal face, and a first passage opening upon the distal face and forming a longitudinal axis,
b) a cannula adapted to advance through the first passage along the longitudinal axis,
c) a first advancement mechanism adapted to advance the cannula through the first passage, d) a probe adapted to advance through the cannula along the longitudinal axis, the probe having a functional element thereon, and e) a second advancement mechanism adapted to advance the probe through the cannula.

In preferred embodiments, the first advancement mechanism is disposed distally in the housing and is adapted to engage the relatively large diameter cannula, while the second advancement mechanism is disposed proximally in the housing and is adapted to engage the relatively small diameter probe.

In use, the cannula is advanced through the patient's skin and into the target tissue. Its position is then fixed. Next, the probe is advanced through the cannula.

In other embodiments, the present invention may be used to first insert a guidewire into the tissue, and then insert a hollow screw over the guidewire.

In preferred embodiments, the first advancement mechanism is disposed distally in the housing and is adapted to engage the relatively small diameter guidewire, while the second advancement mechanism is disposed proximally in the housing and is adapted to engage the relatively large diameter screw.

In use, the guidewire is advanced through the patient's skin and into the target tissue. Its position is then fixed. Next, the screw is advanced over the guidewire to its desired position. Preferably, the second advancement mechanism includes a threaded collar.

In many embodiments, the use of both a rigid probe and a rigid cannula necessarily restricts the location of the functional element to the common longitudinal axis of the cannula and probe. However, in some embodiments, it may be useful to steer the probe so that its functional element can be positioned off the longitudinal axis.

Therefore, in some embodiments, the present invention further comprises a flexible probe and a steerable cannula. In some embodiments, the steerable cannula comprises a laterally-oriented distal opening (i.e. a side opening). The side opening is shaped to steer the distal end of the probe off the longitudinal axis of the cannula. In other embodiments, the steerable cannula comprises a pulls wire. This steerable cannula is adapted so that pulling the pull wire proximally causes the cannula, so that the distal opening thereof becomes offset from the longitudinal axis of the pre-bent cannula.

In preferred procedures beneficially using these steerable embodiments, the distal end of the probe is advanced out of the distal opening of the cannula by the preselected increment, the distal opening of the cannula is rotated by a desired amount, and the distal end of the probe is advanced further out of the distal opening of the cannula by the preselected increment, etc. The stepwise "advance-rotate-advance-rotate" procedure allows the probe to be carefully walked through the tissue, thereby providing access to any region of the target tissue.

In some of the present invention in which the functional element a radially assymetric (i.e., it points in a given direction), the clinician may find that radial location of the functional element is not desirable. Therefore, in some embodiments, simple rotation of the cannula is effected.

In some embodiments, placement of the probe in the vertebral body is achieved by the steps of:

a) advancing both an inner stylet and an outer cannula in order to bore a hole in the vertebral body, b) removing the stylet, c) aligning the distal end of the probe with the proximal opening of the cannula, and d) actuating the device to incrementally advance the probe through the cannula.

FIGS. 17-22 disclose another preferred device 1701 of the present invention. In use of the device of FIGS. 17-22, the clinician first palpates the patient, and locates the appropriate spinal level to be treated. Verification of the appropriate level to be treated will be verified with imaging. Next, the clinician tears the adhesive backing from the mounting plate 1703 to expose the adhesive, and applies the adhesive to area of skin surrounding the entry site.

Next, with the swivel connector 1707 sitting loosely in the distal collet 1709 and lock nut 1711, the clinician orients the swivel connector to provide an appropriate entry angle. The clinician then locks the orientation of the swivel connector by tightening the lock nut upon the collet, which in turns clamps upon the swivel connector.

To attach the housing 1713 to the mounting plate, with lock tab 1715 disposed in an "up" position, the clinician slides the lock tab over proximal end of swivel connector until the lock tab is over the annular recess 1715 of the swivel connector. Next, the clinician presses the lock tab down into a "lock" position, thereby locking the housing to the swivel connector.

Next, the probe is inserted into the housing from the proximal side of the passage 1719 through the tear drop shaped stop (not shown) into the collet 1721. The probe is further advanced through the collet into sleeve 1722 until the probe just begins to protrude out the distal end of the passage. To advance the probe, the clinician squeezes the trigger handle 1723, causing the handle to pivot about the upper pivot pin 1725. As it pivots about this pin, the proximal portion of the sleeve collar in the front is drawn backward into contact with the collar. Because the collet has a tapered distal nose (not shown) that fits with a corresponding taper (not shown) on the proximal end of the sleeve, the collet is forced to clamp down on the probe as it is driven backward. Once the collet is fully clamped on the probe, the handle will then begin to pivot about the second pivot pin 1727. Once the handle begins to move about this second pivot pin, the collet and collar will move forward in unison thus advancing the probe.

Figure 26:
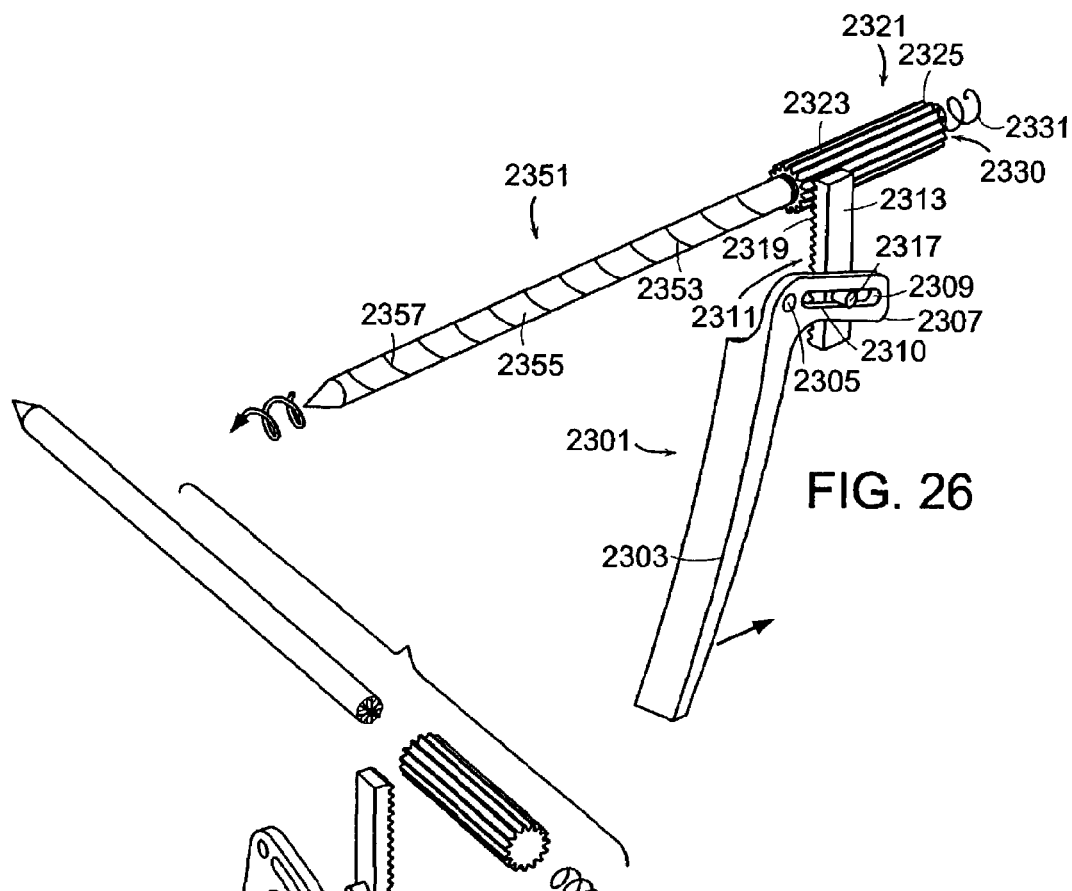
FIG. 26 discloses a perspective view of a preferred rack and pinion advancement mechanism having a probe attached thereto.
Figure 27:
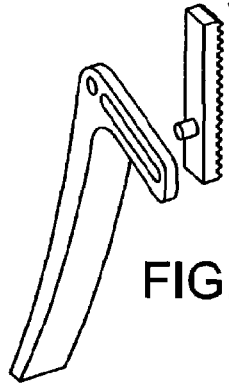
FIG. 27 disclosed an exploded view of the rack and pinion of FIG. 26.
Figure 28:
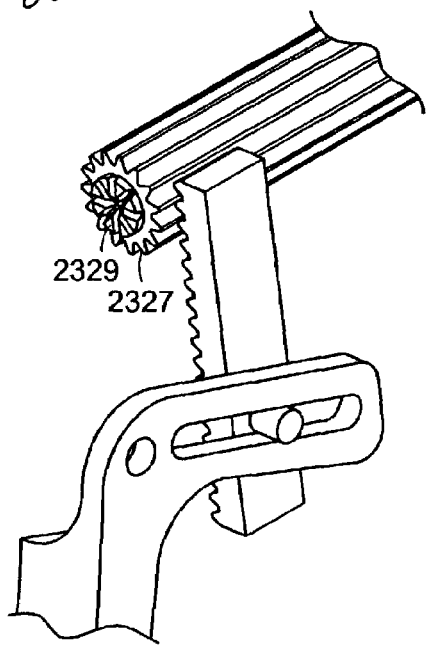
FIG. 28 discloses a perspective close up of the advancement mechanism of FIG. 23.

Now referring to FIGS. 26-28, there is provided an embodiment of an advancement mechanism adapted for simultaneously driving and rotating a probe 2351 having longitudinal rod section 2353 having an outer surface 2355 having a helical thread 2357 formed thereon and a proximal face having driving teeth thereon.

In particular, the advancement mechanism of FIGS. 26-28 comprises:

a) a lever 2301 comprising a distal handle portion 2303, an intermediate pivot 2305 and a proximal portion 2307 having a transverse through hole 2309 forming a lower surface 2310, b) a rack 2311 having a first side 2313 and a second opposing side 2315, the first side having a pin 2317 extending therefrom adapted to fit within the transverse through hole, the second side having a first plurality of gear teeth 2319 extending in the direction of the longitudinal axis of the probe, c) a cylindrical pinion gear 2321 comprising:

i) an outer surface 2323 forming a second plurality of gear teeth 2325 adapted to mate with the first plurality of gear teeth, ii) a distal face 2327 having driving teeth 2329 formed thereon adapted to mate with the driving teeth of the probe, and iii) a proximal face 2330, and d) a compression spring 2331 having a distal end 2333 positioned in contact with the proximal face of the pinion gear.

Prior to use, the compression spring is substantially compressed so that its expansion to cause the pinion to move distally.

In use, the handle portion of the lever is moved proximally, thereby causing the proximal portion to pivot counterclockwise about the pivot. This counterclockwise movement causes the lower surface 2310 to push pin 2317 upwards. This upwards movement causes the rack's gear teeth to impart rotation of the pinion. The drive teeth of the pinion impart the same rotation to the probe, and the helical threads of the probe bite into the tissue during the rotation, thereby causing forward (distal) movement of the probe. When the probe moves forward significantly, expansion of the compression spring prevents any space from opening up between the proximal end of the probe and the distal end of the pinion. A conventional spring return may be used to return the lever and rack to their original positions.

In other embodiments, the probe may have a distal flat cutting face, such as those provided on a trocar. As the probe is rotated, the cutting face cuts out a volume of bone, thereby producing a space in front of the distal end of the probe. The compression spring expands to move the probe forwards into the space so produced.

Now referring to FIGS. 23-25, there is provided an embodiment of an advancement mechanism adapted for simultaneously driving and rotating a probe 2451 having longitudinal rod section 2453 having an outer surface 2455.

In particular, the advancement mechanism of FIGS. 23-25 comprises:

a) a lever 2401 having a lower handle portion 2403 and an upper portion 2405 having first 2406 and second 2407 arms extending therefrom defining a transverse throughhole 2402 therebetween, each arm having lower bias portion 2402 and an upper first lateral pivot hole 2408, b) a U-shaped drive 2411 comprising:
i) an upper portion 2413 pivotally attached to the upper pivot holes of the lever,
ii) a middle curved portion 2415 having first and second arms 2417 defining a transverse throughhole 2418 therethrough, each arm having a distal bias portion 2419,
iii) a lower portion 2421 connected to each arm of the middle portion and having a second lateral pivot hole 2423, c) a collet 2431 disposed through the transverse throughhole of the U-shaped drive, the collet having:
i) a throughbore 2432 adapted to receive a probe,
ii) a distal end 2433 having a hemispherical outer surface and a longitudinal slot 2435 therein,
iii) an outer surface 2439 having an annular ring 2441 extending therefrom, the ring adapted to contact the bias member of the middle curved portion of the U-shaped drive, d) a sleeve 2451 disposed distal of the collet, the sleeve having:
i) an inner bore 2453 adapted to receive a probe,
ii) a proximal end 2455 having a shape adapted for receiving with the hemispherical outer surface of the collet,
iii) an outer surface 2457 having a distal helical groove 2459 and a proximal annular ring 2461 adapted to contact the bias member of the lever.

In use, movement of the handle in the proximal direction causes the pivoting at the first pivot to move U shaped drive in the distal direction. The distal movement of the U-shaped drive causes the rear portion of the U-shaped drive to push against the outside surface of the collet, thereby clamping the collet onto the probe.

Once the collet clamp closes, continued proximal movement of the handle causes the U-shaped drive to pivot about the second pivot, and thereby causing both the collet and sleeve to move distally. As the collet and sleeve move distally, the groove disposed on the outside surface of the sleeve will engage a pin (not shown) disposed on the housing. Engagement of these pins coupled with the forward movement of the sleeve will create rotation of the sleeve and the probe contained therein.

The devices of the present invention may be suitably used for insertion into any tissue in the human body. In some embodiments, the tissue is a soft tissue. In other embodiments, the tissue is a hard tissue. In some embodiments, the hard tissue is cartilage. In some embodiments, the hard tissue is bone. In preferred embodiments when bone is selected as the tissue of choice, the bone is a vertebral body. Preferably, the present invention is adapted to puncture the hard cortical shell of the bone and penetrate at least a portion of the underlying cancellous bone. In some embodiments, the probe advances into the bone to a distance of at least ⅓ of the cross-section of the bone defined by the advance of the probe. In some embodiments, the procedure is an open procedure. In preferred embodiments, the procedure is a percutaneous procedure. In some embodiments, the bone is healthy bone (i.e., non-tumorous).

Typically, the components of the present invention can be made out of any material commonly used in instruments used in surgical procedures, including hardened stainless steel alloys, such as Custom 455 Stainless, available from Carpenter Specialty Alloys of Wyomissing, Pa. If the device is designed to be reusable, then it is preferred that all the components be made of stainless steel. If the device is designed to be disposable, then it is preferred that some of the components be made of plastic.

Preferably, at least the probe component of the device is furnished in a sterilized form. More preferably, the entire device is furnished in a sterilized form.

EXAMPLE

First, the patient is positioned in a prone position. The skin is then prepared with an iodine scrub. The skin entry is then planned and a fluoroscopic picture taken to verify the level of entry.

Next, the clinician palpates the area, locates the device and sets the angle of entry.

In preferred embodiments of using the present invention, referring to FIGS. 1-3, the patch disposed on the proximal face of the housing is removed, thereby exposing an adhesive. The device is placed on the patient's skin above the spine at the target area and the adhesive is pressed onto the skin.

Next, the clinician grasps device and squeezes the lever and grip together. This actuation causes ratchet wheel fixedly attached to the lever to move counterclockwise (i.e., in the direction of arrow B). The second set of teeth disposed on the wheel also move in the counterclockwise direction, thereby causing the first plurality of teeth in engagement therewith (and therefor the entire probe) to move distally by a predetermined increment.

Next, the clinician releases the lever. This release causes a spring (not shown) to return the lever to its original position shown in FIG. 2.

The clinician continues to actuate the device to incrementally advance of the probe until the electrode reaches the desired location in the vertebral body.

Last, the clinician activates the electrode to therapeutically treat the vertebral body.

In addition to the benefits described above provided by the devices of the present invention, the devices are further adapted to provide imaging benefits.

As noted above, in some conventional procedures that penetrate bone, such as the treatment of BVNs, the step of advancing the probe having an electrode is performed under real time imaging, thereby posing possible safety concerns. These safety concerns have lead some clinician, such as those performing vertebroplasty, to advance the device into bone only when the imaging device is turned off, thereby leading to possibly imprecise positioning of the probe's functional element.

The present invention allows the clinician to safely and accurately positioning the probe in bone. In some embodiments, this is accomplished by advancing the probe in known increments under dark conditions. Therefore, the clinician can view the images of the probe and bone, determine from the image the distance that the probe must advance, inactivate the imaging device, and advance the probe by the predetermined increment under dark conditions.

Therefore, in accordance with the present invention, there is provided a method of positioning a probe within tissue, comprising the steps of:
  a) positioning a probe comprising a functional element at a first location in a tissue,
  b) activating an imaging device to locate the location of the probe,
  c) deactivating the imaging device, and
  d) advancing the probe in predetermined increments to a second location in a tissue while the imaging device is inactivated.

There is also provided a method of positioning a probe within tissue, comprising the steps of:
  a) advancing a probe comprising a functional element in predetermined increments from a first location in a tissue to a second location in the absence of imaging guidance.

Also in accordance with the present invention, there is provided a method of positioning a probe within tissue, comprising the steps of:
  a) positioning a probe comprising an electrode at a first location in a tissue,
  b) activating an imaging device to locate the location of the probe,
  c) deactivating the imaging device, and
  d) advancing the probe to a second location in a tissue while the imaging device is inactivated.

In addition, the present invention provides the clinician with an ability to advance the probe while standing outside of the radiation field produced by the imaging device. In particularly, all of the advancement means of the devices of the present invention can be equipped with a remote advancement means, such as a flexible cable with a housing used to transmit torque, that allows the clinician to activate the advancement means while standing outside of the radiation field produced by the imaging device. For example, in FIGS. 9 and 10A, the rod 203 can be provided in the form of a long flexible cable which, when turned, turns the rotatable cylinder 211.

Therefore, in accordance with the present invention, there is provided a method of positioning a probe within hard tissue, comprising the steps of:
  a) positioning a probe comprising a functional element at a first location in the hard tissue,
  b) activating an imaging device to locate the location of the probe, thereby producing an imaging field,
  c) advancing the probe to a second location in the tissue from a remote location.

Another advantage of the present invention associated with imaging is that the clinician no longer needs to use protective gear associated with direct imaging such as draping and shields. Since the present invention allows the clinician to precisely locate the probe via either intermittent imaging and/or remote actuation of the advancement mechanism, the necessity of using radiation protective gear such as draping and shields is reduced.

We claim:

1. A device for therapeutically treating bone, comprising:
  a) a housing having a base portion, a distal face and a first passage opening onto the distal face and forming a longitudinal axis,
  b) a probe adapted to advance through the first passage along the longitudinal axis, the probe having a functional element thereon, the probe having a distal end portion having a sharp tip shaped to pierce cortical bone,
  c) an advancement mechanism adapted to advance the probe through the first passage, and
  d) an anchor rotatably attached to the distal face of the housing and adapted to provide rotation of the housing about the longitudinal axis, wherein the anchor comprises:
    a plate comprising:
      i) a proximal face,
      ii) a distal face,
      iii) a first throughhole extending from the proximal face to the distal face, wherein at least a portion of the throughhole forms a portion of a substantially spherical recess, and
      iv) a second different throughhole extending from the proximal face to the substantially spherical recess, wherein the throughholes have separate proximal openings,
    a bearing comprising:
      i) a substantially spherical portion disposed in the substantially spherical recess; and
    a lock screw inserted into the second throughhole of the plate and fixing the orientation of the bearing.

2. The device of claim 1 wherein anchor has a distal face adapted to attach to skin.

3. The device of claim 1 wherein the anchor has a distal face adapted for bony fixation.

4. The device of claim 1 wherein the anchor has a distal face adapted to attach to an external apparatus.

5. The device of claim 1 wherein the anchor has a distal face comprising an adhesive.

6. The device of claim 1 wherein the plate further comprises an annulus extending proximally from the proximal face, formed around the throughhole.

7. The device of claim 6 wherein the annulus has a laterally extending proximal lip.

8. The device of claim 7 wherein the housing further comprises a recess adapted to receive the lip of the annulus.

9. The device of claim 8 wherein the anchor and recess are adapted so that the housing can be at least partially rotated about the first throughhole.

10. The device of claim 8 wherein the recess has a shape comprising a portion of a sphere.

11. The device of claim 1 wherein the bearing further comprises:
   ii) an annulus formed upon the proximal portion of the bearing and further having a proximal end portion and a laterally extending proximal lip, and
   iii) a third throughhole extending from the distal portion of the substantially spherical portion to the proximal portion of the annulus, defining a proximal opening and a distal opening.

* * * * *